US012248520B2

(12) United States Patent
Sakakibara et al.

(10) Patent No.: US 12,248,520 B2
(45) Date of Patent: Mar. 11, 2025

(54) INFORMATION PROCESSING SYSTEM, INFORMATION PROCESSING METHOD, AND PROGRAM

(71) Applicant: TOYOTA JIDOSHA KABUSHIKI KAISHA, Toyota (JP)

(72) Inventors: Kiyomi Sakakibara, Iwakura (JP); Shintaro Yoshizawa, Nagoya (JP); Yuhei Yamaguchi, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 722 days.

(21) Appl. No.: 17/532,517

(22) Filed: Nov. 22, 2021

(65) Prior Publication Data

US 2022/0160923 A1     May 26, 2022

(30) Foreign Application Priority Data

Nov. 26, 2020   (JP) .................... 2020-195979

(51) Int. Cl.
*G06F 16/9035*     (2019.01)
*G06F 16/906*     (2019.01)

(52) U.S. Cl.
CPC ........ *G06F 16/9035* (2019.01); *G06F 16/906* (2019.01)

(58) Field of Classification Search
None
See application file for complete search history.

(56) References Cited

U.S. PATENT DOCUMENTS

| | | | | |
|---|---|---|---|---|
| 2005/0266102 A1* | 12/2005 | Bahash | ................... | A23L 27/00 702/19 |
| 2008/0131858 A1* | 6/2008 | Gordon | ............. | G09B 19/0076 434/327 |
| 2010/0169340 A1* | 7/2010 | Kenedy | ............. | G06Q 30/0631 707/758 |

(Continued)

FOREIGN PATENT DOCUMENTS

| JP | 2019-170692 A | 10/2019 |
|---|---|---|
| JP | 6665899 B2 | 3/2020 |

(Continued)

*Primary Examiner* — Khanh B Pham
*Assistant Examiner* — Navneet Gmahl
(74) *Attorney, Agent, or Firm* — Dinsmore & Shohl LLP

(57) ABSTRACT

The information processing system includes a classification unit, an acquisition unit, a selection unit, an evaluation unit, and a generation unit. The classification unit classifies a plurality of fragrances into segments defined corresponding to a combination of one of first classification items on a first classification axis with one of second classification items on a second classification axis. The acquisition unit accepts input of information related to the first classification axis from the target person. The selection unit determines one of the first classification items based on the information and selects a fragrance for evaluation from each of segments that correspond to the first classification item and whose second classification items differ from each other. The evaluation unit acquires, for each of the fragrances for evaluation, evaluation information of a scent from the target person. The generation unit generates information on the fragrance for presentation based on the evaluation information.

14 Claims, 20 Drawing Sheets

(56) References Cited

U.S. PATENT DOCUMENTS

| | | | |
|---|---|---|---|
| 2012/0125082 A1* | 5/2012 | Sugiyama | G01N 33/5308 |
| | | | 73/23.34 |
| 2016/0132950 A1* | 5/2016 | Fleming | G06Q 30/0621 |
| | | | 705/26.5 |
| 2017/0140252 A1* | 5/2017 | Stucki | G06F 18/24 |
| 2018/0186904 A1* | 7/2018 | Lee | C08F 210/14 |
| 2019/0019033 A1* | 1/2019 | Chang | G06V 20/41 |
| 2019/0370878 A1* | 12/2019 | Tran | G06Q 30/0203 |
| 2020/0098029 A1* | 3/2020 | Shoji | G06Q 30/0627 |
| 2021/0000999 A1* | 1/2021 | Kitagawa | G06V 20/52 |
| 2021/0128868 A1* | 5/2021 | Matsumoto | G16H 20/70 |
| 2021/0248664 A1* | 8/2021 | Maeda | G06Q 30/0282 |
| 2022/0261876 A1* | 8/2022 | Maeda | G06Q 30/0641 |
| 2023/0221293 A1* | 7/2023 | Fujita | G06Q 50/10 |
| | | | 73/23.2 |

FOREIGN PATENT DOCUMENTS

| | | |
|---|---|---|
| JP | 6763621 B1 | 9/2020 |
| WO | 2018/163361 A1 | 9/2018 |

\* cited by examiner

| | | PURPOSE OF USE | | |
|---|---|---|---|---|
| | | C1 | C2 | C3 |
| | | COMFORT | RELAXING | REFRESHING |
| SMELL QUALITY | R1 CITRUS | GRAPEFRUIT ESSENTIAL OIL | ORANGE ESSENTIAL OIL | GRAPEFRUIT ESSENTIAL OIL |
| | R2 TREE | FRANKINCENSE ESSENTIAL OIL (OLIBANUM/MASTIC) | FRANKINCENSE ESSENTIAL OIL (OLIBANUM/MASTIC) | FRANKINCENSE ESSENTIAL OIL (OLIBANUM/MASTIC) |
| | R3 FLORAL | LAVENDER ESSENTIAL OIL | LAVENDER ESSENTIAL OIL | GERANIUM ESSENTIAL OIL |
| | R4 SWEET | ETHYL VANILLIN | ETHYL VANILLIN | PERUVIAN BALSAM ESSENTIAL OIL |
| | R5 HERB/MINT | PEPPERMINT ESSENTIAL OIL | EUCALYPTUS ESSENTIAL OIL | PEPPERMINT ESSENTIAL OIL |

Fig. 2

| | | PURPOSE OF USE | | |
|---|---|---|---|---|
| | | C1 | C2 | C3 |
| | | COMFORT | RELAXING | REFRESHING |
| SMELL QUALITY | R1 CITRUS | FRAGRANCE110 : M1=9<br>FRAGRANCE111 : M1=7<br>FRAGRANCE112 : M1=8 | FRAGRANCE210 : M2=6<br>FRAGRANCE211 : M2=7<br>FRAGRANCE212 : M2=8 | FRAGRANCE310 : M2=7<br>FRAGRANCE311 : M2=7<br>FRAGRANCE312 : M2=8 |
| | R2 TREE | FRAGRANCE120 : M1=7<br>FRAGRANCE121 : M1=8<br>FRAGRANCE122 : M1=6 | ... | ... |
| | R3 FLORAL | FRAGRANCE130 : M1=5<br>FRAGRANCE131 : M1=4<br>FRAGRANCE132 : M1=6 | ... | ... |
| | R4 SWEET | FRAGRANCE140 : M1=4<br>FRAGRANCE141 : M1=7<br>FRAGRANCE142 : M1=6 | ... | ... |
| | R5 HERB/MINT | FRAGRANCE150 : M1=4<br>FRAGRANCE151 : M1=4<br>FRAGRANCE152 : M1=5 | ... | ... |

Fig. 6

INFORMATION PROCESSING SYSTEM, INFORMATION PROCESSING METHOD, AND PROGRAM

CROSS REFERENCE TO RELATED APPLICATIONS

This application is based upon and claims the benefit of priority from Japanese patent application No. 2020-195979, filed on Nov. 26, 2020, the disclosure of which is incorporated herein in its entirety by reference.

BACKGROUND

The present disclosure relates to an information processing system, an information processing method, and a program for presenting a scent in accordance with a target person.

A technique for automatically presenting an appropriate scent according to personal preference or a situation of a person without the need for expert knowledge or know-how has been proposed. For example, Japanese Patent No. 6665899 discloses a scent-presentation-information output system that classifies a user into one of clusters based on scent evaluation information input by the user and recommends a scent in accordance with the classification.

SUMMARY

However, in the system disclosed in Japanese Patent No. 6665899, when the number of kinds of scents to be evaluated is small or when scents of similar kinds are to be evaluated, it is difficult to classify users into appropriate clusters. On the other hand, if a number of kinds of scents are to be evaluated in order to classify users into appropriate clusters, it will take a lot of time for this evaluation to be made, which will increase the burden on the user.

The present disclosure has been made in order to solve the aforementioned problem, and the aim of the present disclosure is to provide an information processing system, an information processing method, and a program capable of presenting a scent in accordance with individual differences in the preferences and responses of a target person more appropriately with a small burden.

An information processing system according to one aspect of the present disclosure presents a scent to a target person. The information processing system includes a classification unit, an acquisition unit, a selection unit, an evaluation unit, and a generation unit. The classification unit classifies a plurality of fragrances into segments defined corresponding to a combination of one of first classification items on a first classification axis with one of second classification items on a second classification axis. The acquisition unit accepts input of information related to the first classification axis from the target person. The selection unit determines one of the first classification items based on the information related to the first classification axis and selects at least one fragrance for evaluation from each of segments that correspond to the first classification item and whose second classification items differ from each other. The evaluation unit acquires, for each of the fragrances for evaluation that have been selected, evaluation information of a scent from the target person. The generation unit generates information on the fragrance for presentation based on the evaluation information. According to the aforementioned configuration, the target person only needs to actually evaluate fragrances narrowed down to a small number based on the first classification item, which reduces the evaluation burden on the target person. Further, the information processing system is able to appropriately select fragrances for presentation in accordance with individual differences in the preferences and responses of a target person from among the fragrances whose second classification items differ from each other and whose variety is ensured and present the selected fragrances to the target person.

The first classification item may be items related to the purpose of using a fragrance. Accordingly, the fragrances can be appropriately classified in accordance with the purpose of use. Further, the second classification items may be items related to a smell quality of a fragrance. Accordingly, variety of fragrances for evaluation can be ensured.

The classification unit may determine, for each of the plurality of fragrances, a first classification item of the fragrance based on degrees of matching of the fragrance with the respective items on the first classification axis. Then the classification unit may determine, for each of the segments, the fragrance having the highest degree of matching with the first classification item that corresponds to the segment as an expression scent that represents the segment, among the fragrances classified into the segment. The selection unit may select expression scents determined for the respective segments that correspond to the first classification item determined based on the information related to the first classification axis and whose second classification items differ from each other to be the fragrances for evaluation. Accordingly, variety of fragrances for evaluation are ensured more definitely, and the information processing system is able to more appropriately select a fragrance for presentation and present the selected fragrance to a target person.

Further, the selection unit may select an expression scent whose degree of matching with the first classification item determined based on the information related to the first classification axis is equal to or higher than a predetermined threshold to be the fragrance for evaluation. Accordingly, it is possible to reduce the number of fragrances for evaluation evaluated by the target person and thus further reduce the evaluation burden.

Further, the evaluation information may include evaluation scores, and the evaluation unit may cause the target person to input evaluation scores of fragrances for evaluation from a fragrance for evaluation having the highest degree of matching with the first classification item determined based on the information related to the first classification axis in order. Then the evaluation unit may interrupt acceptance of input of the evaluation information when the evaluation score is lower than a predetermined threshold or when the evaluation score is lower than an evaluation score of a fragrance for evaluation that has been input just before this evaluation score is input by a predetermined threshold or more. Accordingly, by causing the evaluation by the target person to be ended early, the evaluation burden on the target person can be further reduced.

The evaluation information may include evaluation scores, and the evaluation unit may determine a fragrance for evaluation having the evaluation score equal to or higher than a predetermined threshold to be the fragrance for presentation. Further, the evaluation unit may determine a fragrance in which fragrances for evaluation having evaluation scores equal to or higher than a predetermined threshold are blended with each other in accordance with the evaluation score to be the fragrance for presentation.

Accordingly, the information processing system is able to present a scent that is more suitable for the target person.

The evaluation unit may estimate evaluation information of a scent from biological information of the target person. Accordingly, the evaluation processing may be performed even when the target person does not input evaluation scores, whereby the evaluation burden on the target person can be reduced. Further, the information processing system is able to improve the accuracy of the evaluation by using biological information including unconscious physiological reactions, and more appropriately select a fragrance for presentation.

An information processing method according to one aspect of the present disclosure is a method of presenting a scent to a target person. The information processing method includes a classification step, an acquisition step, a selection step, an evaluation step, and a generation step. The classification step is a step of classifying a plurality of fragrances into segments defined corresponding to a combination of one of first classification items on a first classification axis with one of second classification items on a second classification axis. The acquisition step is a step of accepting input of information related to the first classification axis from the target person. The selection step is a step of determining one of the first classification items based on the information related to the first classification axis and selecting at least one fragrance for evaluation from each of segments that correspond to the first classification item and whose second classification items differ from each other. The evaluation step is a step of acquiring, for each of the fragrances for evaluation that have been selected, evaluation information of a scent from the target person. The generation step is a step of generating information on a fragrance for presentation to be presented to the target person based on the evaluation information. According to the aforementioned configuration, the target person only needs to actually evaluate fragrances narrowed down to a small number based on the first classification item, which reduces the evaluation burden. Further, it is possible to appropriately select fragrances for presentation in accordance with individual differences in the preferences and responses of a target person from among the fragrances whose second classification items differ from each other and whose variety is ensured and present the selected fragrances to the target person.

A program according to an aspect of the present disclosure is a program for presenting a scent to target person. The program causes a computer to execute classification processing, acquisition processing, selection processing, evaluation processing, and generation processing. The classification processing is processing for classifying a plurality of fragrances into segments defined corresponding to a combination of one of first classification items on a first classification axis with one of second classification items on a second classification axis. The acquisition processing is processing for accepting input of information related to the first classification axis from the target person. The selection processing is processing for determining one of the first classification items based on the information related to the first classification axis and selecting at least one fragrance for evaluation from each of segments that correspond to the first classification item and whose second classification items differ from each other. The evaluation processing is processing for acquiring, for each of the fragrances for evaluation that have been selected, evaluation information of a scent from the target person. The generation processing is processing for generating information on a fragrance for presentation to be presented to the target person based on the evaluation information. According to the aforementioned configuration, the target person only needs to actually evaluate fragrances narrowed down to a small number based on the first classification item, whereby the evaluation burden is reduced. Further, it is possible to appropriately select fragrances for presentation in accordance with individual differences in the preferences and responses of a target person from among the fragrances whose second classification items differ from each other and whose variety is ensured and present the selected fragrances to the target person.

According to the present disclosure, it is possible to provide an information processing system, an information processing method, and a program capable of presenting a scent in accordance with individual differences in the preferences and responses of a target person more appropriately with a small burden.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 2 is a diagram for describing one example of a classification table according to the first embodiment;

FIG. 6 is a diagram for describing processing of classifying fragrances according to the first embodiment;

DESCRIPTION OF EMBODIMENTS

Figure 1:
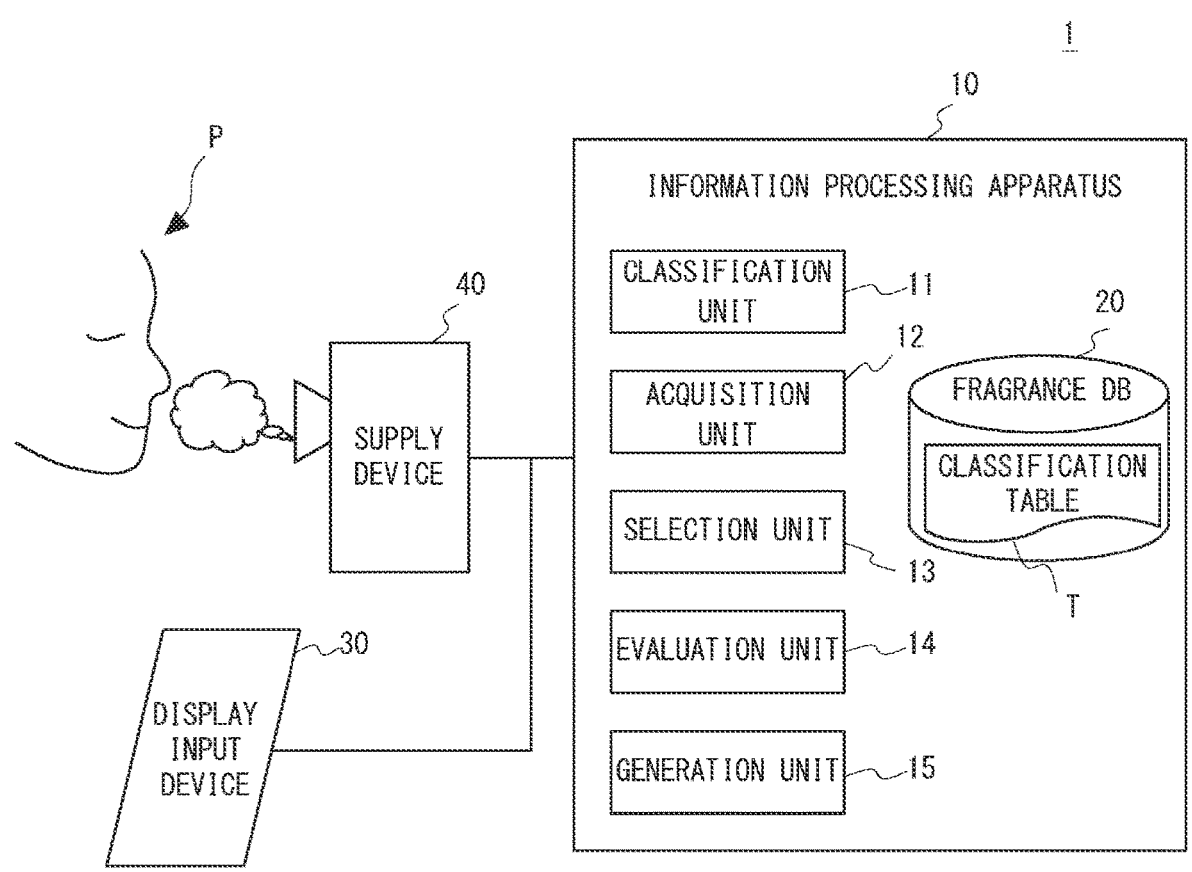
FIG. 1 is a schematic configuration diagram of a scent presentation system according to a first embodiment.

Hereinafter, although the present disclosure will be described with reference to embodiments of the present disclosure, the present disclosure according to claims is not limited to the following embodiments. For the clarification of the description, the following description and the drawings are omitted and simplified as appropriate. Throughout the drawings, the same components are denoted by the same reference signs and repeated descriptions will be omitted as appropriate.

Problems Solved by Embodiments

Here, problems solved by embodiments will be described in further detail.

In recent years, custom-made fragrances in accordance with personal preferences or situations have been focused on. For example, a service in which a target person smells various kinds of fragrances or fragrances containing them, determines a scent recipe that suits his/her preference and usage scene, and purchases the fragrance of the original recipe on the spot has been proposed. In order to appropriately determine the scent recipe, however, expert advice is necessary. When there is a change in the climate when a scent is used or the purpose of using a scent, he/she needs to consult with an expert every time such a change occurs. Professional knowledge or know-how is also required when a sample fragrance is selected to study the tendency of preference of a target person or when information on personal preferences or responses is to be grasped. It has been required to provide a scent presentation apparatus that automatically presents an appropriate scent in accordance with personal preferences or situations without the need for expert knowledge or know-how.

For example, a method of changing the concentration or kinds of scents based on a stress load caused by a scent, which is detected according to the skin temperature, has been proposed. It is known that scent induces emotional and physiological responses, and thus it is expected that scent will improve comfort, the relaxation level, and psychosomatic revitalization (refreshing). In addition, there are two types of emotions recalled by scent: inborn emotion and emotion formed by experience, memory, knowledge, etc., and the latter emotion, in particular, varies among people. Therefore, it is difficult to predict personal preferences or physiological and/or psychological responses in advance. Therefore, in this method, while it is possible to select a scent with a low stress load, it is difficult to select a suitable scent that sufficiently matches individual differences in physiological and psychological responses to the scent.

Further, a method of classifying a user into one of clusters based on scent evaluation information input by the user and recommending a scent in accordance with the classification has been proposed, as disclosed in Japanese Patent No. 6665899 mentioned above. However, when the number of kinds of scents to be evaluated is small or when scents of similar kinds are to be evaluated, it is difficult to classify users into appropriate clusters. On the other hand, if a number of kinds of scents are to be evaluated in order to classify users into appropriate clusters, it will take a lot of time for evaluation to be made, which will increase the burden on the user. In addition, there is a wide variety of scent substances. When the kinds of scent substances and a form in which they are blended (e.g., blend ratio) are taken into account, it can be said that there are almost an infinite number of scents. There is currently no system for quantitatively expressing the smell sensation (i.e., olfaction) that corresponds to the three primary colors of vision, nor is there unified standard for the classification of scents. The above Japanese Patent No. 6665899 also does not disclose what scents are to be evaluated and how to present the scents when users are classified into clusters.

As described above, the current scent presentation apparatus has problems in terms of the burden on the target person to whom scents will be presented and appropriateness. The present disclosure has been made in order to solve this problem, and embodiments will be described below.

First Embodiment

First, with reference to FIGS. 1 to 14, a first embodiment will be described. FIG. 1 is a schematic configuration diagram of a scent presentation system 1 according to the first embodiment. The scent presentation system 1 is a computer system for presenting a scent in accordance with a target person P to the target person P. The scent presentation system 1 is installed, for example, in a store, an accommodation facility or the like. The scent presentation system 1 includes an information processing apparatus (information processing system) 10, a display input device 30, and a supply device 40.

The information processing apparatus 10 is a computer apparatus that performs information processing for presenting a scent in accordance with the target person P to the target person P. The information processing apparatus 10 is connected to the display input device 30 and the supply device 40. The information processing apparatus 10 causes the target person P to evaluate each of fragrances for evaluation via the supply device 40 in accordance with acquisition of information related to a first classification axis that will be described later via the display input device 30. The information processing apparatus 10 determines fragrances for presentation presented to the target person P based on the results of the evaluation and presents the fragrances for presentation to the target person P via the display input device 30 or the supply device 40.

The display input device 30 is a display input device such as a touch panel. The display input device 30 accepts input from the target person P and supplies the accepted information to the information processing apparatus 10. Further, the display input device 30 displays the information supplied from the information processing apparatus 10. Note that the display input device 30 may be formed of a display device such as a display and an input device such a mouse or a keyboard.

The supply device 40 is a dispenser that includes therein a plurality of fragrances and generates scents using one or more fragrances selected from a plurality of fragrances included in the supply device 40. The supply device 40 discharges or sprays (supplies) fragrances for evaluation based on control from the information processing apparatus 10. Further, the supply device 40 supplies the fragrances for presentation based on the control from the information processing apparatus 10.

Next, a functional configuration of the information processing apparatus 10 will be described. The information processing apparatus 10 includes a classification unit 11, an acquisition unit 12, a selection unit 13, an evaluation unit 14, a generation unit 15, and a fragrance database (DB) 20.

The classification unit 11 is connected to the fragrance DB 20 and classifies a plurality of fragrances into segments defined by a plurality of classification axes based on the data stored in the fragrance DB 20. The plurality of fragrances include natural fragrances, synthetic fragrances, or compound fragrances. The classification axes are evaluation axes for classifying fragrances. In the first embodiment, the segments are defined corresponding to a combination of one of first classification items on a first classification axis with one of second classification items on a second classification axis. The first classification item is one of explanatory variables defined along the first classification axis. In some embodiments, the first classification axis and the first classification item are an evaluation axis and an explanatory variable that the target person can objectively recognize and with which fragrances can be appropriately classified. In the first embodiment, the first classification axis relates to the purpose of using the fragrance. Further, the first classification items are items related to the purpose of using a fragrance (the items of the purpose of use), and include, for example, "comfort (purpose)", "relaxing (purpose)", "refreshing (purpose)", "awakening (purpose)" and the like. Accordingly, fragrances can be appropriately classified in accordance with the purpose of use.

The second classification item is one of explanatory variables defined along the second classification axis. In some embodiments, the second classification axis and the second classification item are an evaluation axis and an explanatory variable suitable for ensuring variety of scents. In the first embodiment, the second classification axis is an axis related to smell qualities of fragrances. Further, the second classification items are items that are related to smell qualities of fragrances and may be, for example, "citrus", "tree", "floral", "sweet", "herb/mint" and the like.

The classification unit 11 classifies a plurality of fragrances into segments and generates a classification table T in advance, and stores the classification table T in the fragrance DB 20.

The acquisition unit 12 is connected to the display input device 30 and accepts input of information related to the first classification axis from the target person P via the display input device 30. In the first embodiment, the information related to the first classification axis is the information related to the purpose of use.

The selection unit 13 determines the first classification item of the fragrances for evaluation used in the subsequent processing based on the information related to the first classification axis acquired by the acquisition unit 12. Then, the selection unit 13 selects at least one fragrance for evaluation from each of segments that correspond to the above first classification item and whose second classification items differ from each other using the classification table T.

The evaluation unit 14 is connected to the display input device 30 and the supply device 40 and performs processing for evaluating the fragrances. Specifically, the evaluation unit 14 encourages the target person P to evaluate the selected fragrances for evaluation via the display input device 30. Next, the evaluation unit 14 transmits information on the selected fragrances for evaluation to the supply device 40 and causes the supply device 40 to discharge or spray the fragrances for evaluation. Next, the evaluation unit 14 acquires, for each of the fragrances for evaluation that have been selected, evaluation information of the scents from the target person P via the display input device 30, that is, accepts input of the evaluation information of the scents. Then the evaluation unit 14 determines the fragrances for presentation based on the evaluation information.

The generation unit 15 generates information on the fragrances for presentation that have been determined. The fragrance information may include identification information (ID) of a fragrance, and information on a blend ratio if the fragrance for presentation is a compounded fragrance. The generation unit 15 is connected to the supply device 40, transmits information on the fragrances for presentation to the supply device 40, and causes the supply device 40 to discharge or spray the fragrances for presentation. Further, the generation unit 15 is connected to the display input device 30 and causes the display input device 30 to display information on the fragrances for presentation. In this way, the generation unit 15 is able to present the fragrances for presentation to the target person P.

The fragrance DB 20 is a storage medium that stores information that is required for information processing by the information processing apparatus 10. For example, the fragrance DB 20 stores information on a plurality of fragrances, and this information includes data used for classification processing performed by the classification unit 11. Further, the fragrance DB 20 stores the classification table T generated by the classification unit 11.

Note that the information processing apparatus 10 may further include a sales processing unit (not shown) and perform payment processing for selling fragrances for presentation to the target person P and processing of managing sales information.

Further, while the fragrance DB 20 is included in the information processing apparatus 10 in the first embodiment, the fragrance DB 20 may instead be included in an external device (not shown) connected to the information processing apparatus 10 in such a way that they can communicate with each other.

FIG. 2 is a diagram for describing one example of the classification table T according to the first embodiment. In this first embodiment, the classification table T is a two-dimensional table that is defined by the column which indicates classification items about the purpose of use, which is the first classification axis, and the row which indicates classification items about the smell quality, which is the second classification axis.

In FIG. 2, the classification items of the purpose of use are "comfort", "relaxing", and "refreshing", and the segment groups located in the columns specified by these classification items are referred to as column groups C1-C3.

Further, in FIG. 2, the classification items of the smell quality are "citrus", "tree", "floral", "sweet", and "herb/mint", and the segment groups located in the rows specified by these classification items are referred to as row groups R1-R5. While the number of columns (i.e., the number of column groups) and the number of rows (i.e., the number of row groups) are not limited to those described above, each of them is at least two. Regarding the number of row groups in particular, the greater the number of row groups is, the greater the variety of scents but the greater the evaluation burden on the target person. Therefore, the number of row groups is set to an appropriate number, weighing the benefits of variety against risks of the increase in the evaluation burden. Further, the number of row groups may be set by variety of the fragrances registered in the fragrance DB 20 and the target person to whom the scent is to be presented. For example, when the number of kinds of fragrances registered in the fragrance DB 20 is about 80 and it is intended to present scents to a general user as a target person, the appropriate number of row groups is about 7 (6-8).

For example, the fragrance when the first classification item is "comfort" and the second classification item is "citrus" is "grapefruit essential oil", which is registered in a segment that belongs to the column group C1 and the row group R1 of the classification table T. Further, the fragrance when the first classification item is "comfort" and the second classification item is "tree" is "frankincense essential oil", which is registered in a segment that belongs to the column group C1 and the row group R2.

A fragrance registered in a segment is a fragrance called an expression scent that represents this segment. The expression scent, which suitably expresses the combination of the first classification item and the second classification item of the segment, is selected from among the fragrances classified into the segment (described later).

Figure 3:
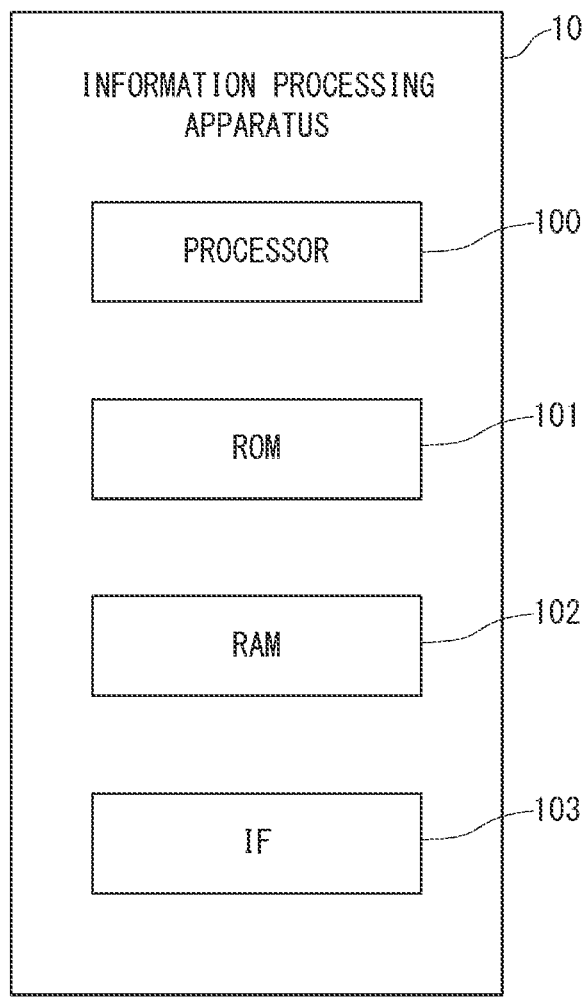
FIG. 3 is a block diagram showing a hardware configuration of an information processing apparatus according to the first embodiment.

FIG. 3 is a block diagram showing a hardware configuration of the information processing apparatus 10 according to the first embodiment.

The information processing apparatus 10 includes, as main hardware configurations, a processor 100, a Read Only Memory (ROM) 101, a Random Access Memory (RAM) 102, and an interface (IF) unit 103. The processor 100, the ROM 101, the RAM 102, and the interface unit 103 are connected to one another via a data bus.

The processor 100 has a function as an arithmetic device that performs control processing, arithmetic processing, etc. The processor 100 may be a Central Processing Unit (CPU), a Graphics Processing Unit (GPU), a field-programmable gate array (FPGA), a digital signal processor (DSP), or an application specific integrated circuit (ASIC) and a combination thereof. The ROM 101 includes a function of storing a control program, an arithmetic program and the like executed by the processor 100. The RAM 102 includes a function of temporarily storing processing data and the like. The interface unit 103 receives and outputs signals from and to the outside via a wire or wirelessly. Further, the interface unit 103 accepts data input operations by a user and displays information for the user. For example, the interface unit 103 communicates with the display input device 30 and the supply device 40.

Figure 4:
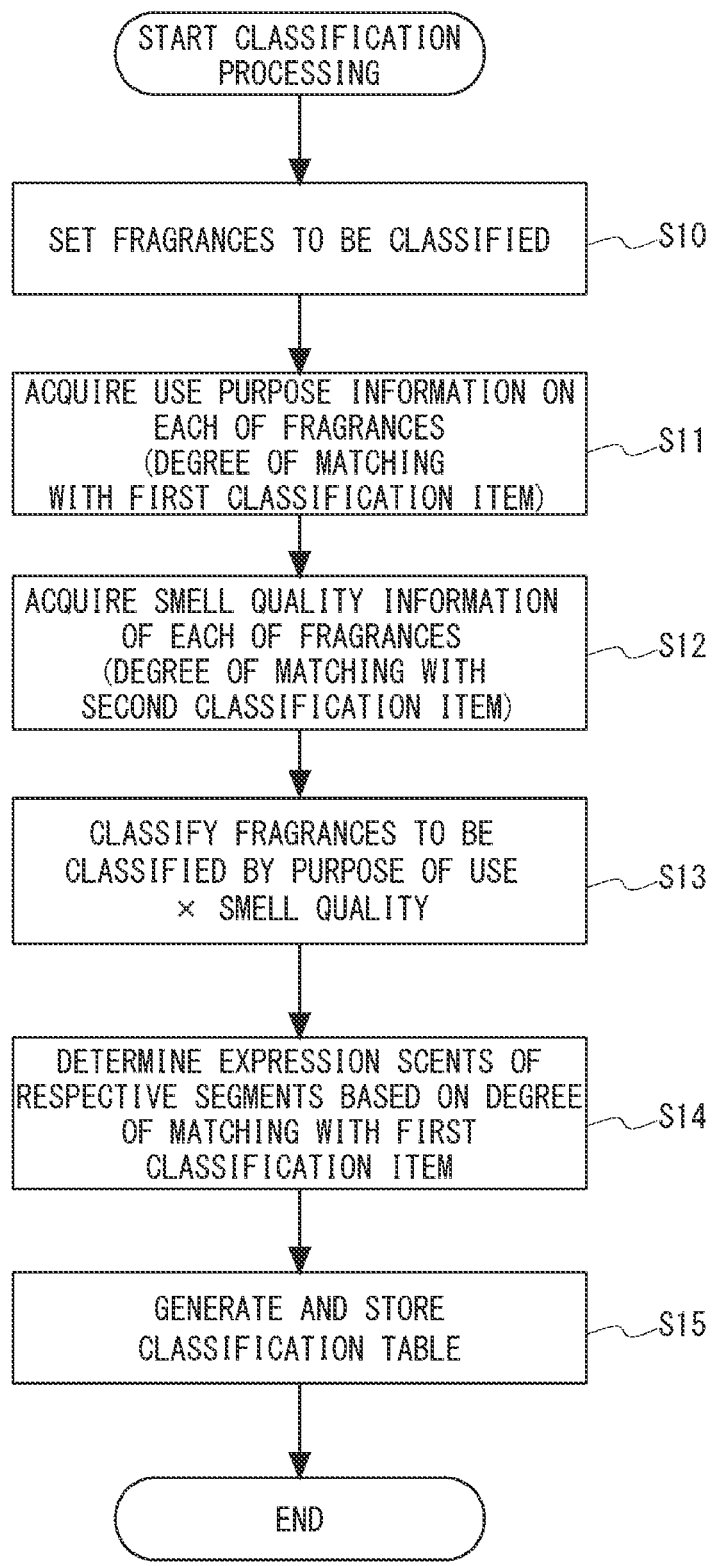
FIG. 4 is a flowchart showing a procedure for classification processing according to the first embodiment.

Referring next to FIG. 4, with reference to FIGS. 5-13, classification processing in the information processing apparatus 10 will be described. FIG. 4 is a flowchart showing a procedure for the classification processing according to the first embodiment. This classification processing is performed prior to the operation of the information processing apparatus 10. In addition thereto, this classification processing may be performed in accordance with information on a fragrance in the fragrance DB 20 being updated during the operation. First, in Step S10 in FIG. 4, the classification unit 11 of the information processing apparatus 10 sets which fragrances are to be classified, that is, sets fragrances to be classified. The classification unit 11 may classify all the fragrances stored in the fragrance DB 20 or only some of the fragrances.

Next, in Step S11, the classification unit 11 acquires the use purpose information of each of the fragrances to be classified from the fragrance DB 20. The use purpose information is information that is generated in advance based on results of evaluating fragrances by a number of examinees based on the purpose of use as the evaluation axis. In this first embodiment, the use purpose information is information on degrees of matching with the respective first classification items.

Figure 5:
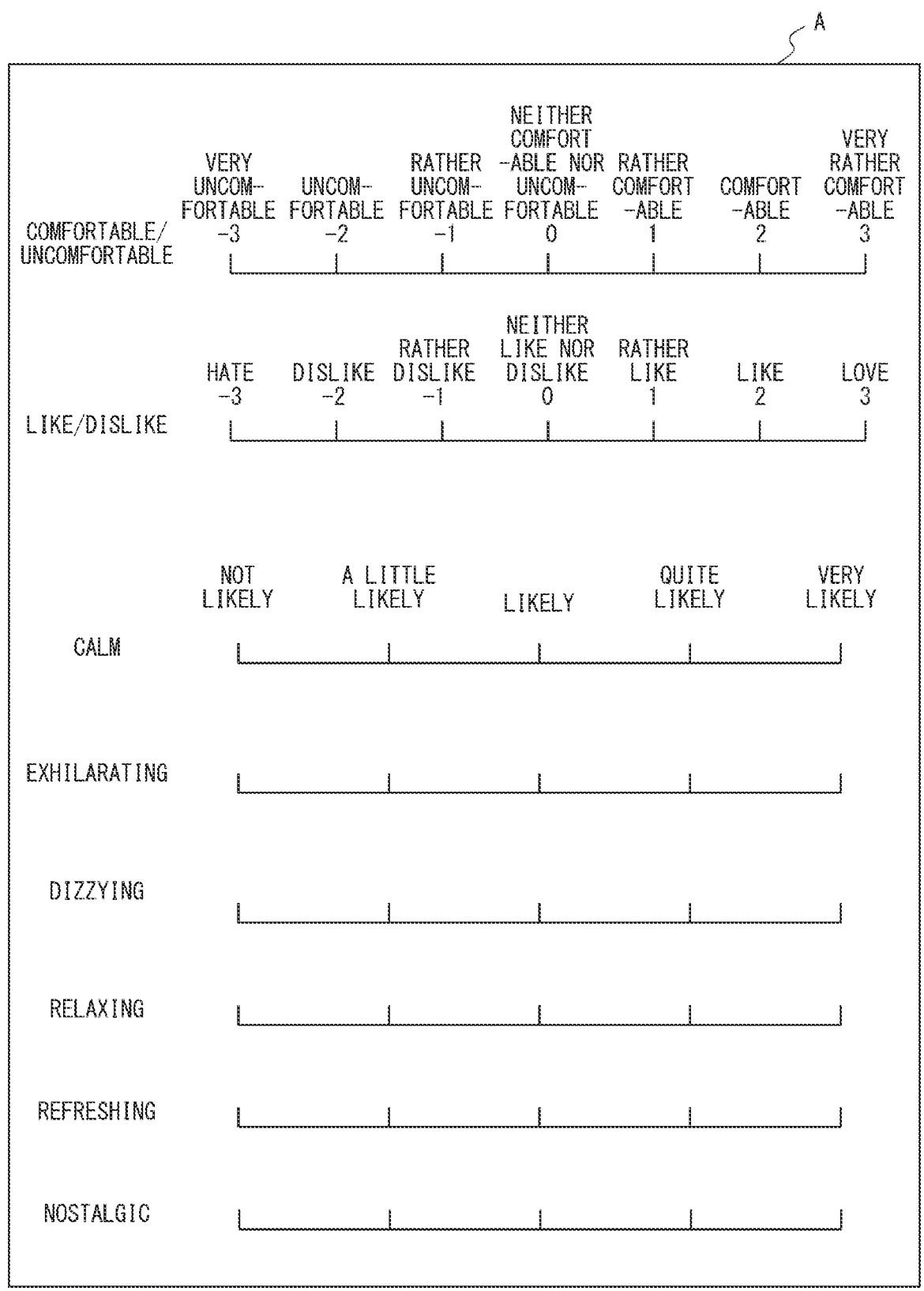
FIG. 5 is a diagram for describing use purpose information according to the first embodiment.

FIG. 5 is a diagram for describing the use purpose information according to the first embodiment. FIG. 5 shows one example of an evaluation sheet A used to evaluate fragrances by a number of examinees based on the purpose of use as the evaluation axis. The purpose of use is closely linked to the emotional evaluation of the fragrance and evaluation items of various emotions are listed in the evaluation sheet A. The evaluation items of emotion are, for example, "comfortable/uncomfortable", "like/dislike", "calm", "exhilarating", "dizzying", "relaxing", "refreshing", "nostalgic" and the like. The evaluation items "comfortable/uncomfortable" and "like/dislike" are related to the first classification item "comfort", the evaluation items "calm" and "relaxing" are related to the first classification item "relaxing", and the evaluation items "exhilarating" and "refreshing" are related to the first classification item "refreshing". An examinee smells a fragrance and inputs, for each of the evaluation items, a score indicating the degree of matching of this fragrance with this evaluation item, thereby evaluating the purpose of using the fragrance. While the degree of matching is shown by seven grades in FIG. 5, this is merely one example. Then the classification unit 11 obtains the average of the degrees of matching with the evaluation item evaluated by a number of examinees and calculates this average value as the degrees of matching with each first classification item. For example, the classification unit 11 may set the average value of the degrees of matching with the evaluation item "comfortable/uncomfortable" as the degree of matching with the first classification item "comfort". Alternatively, the classification unit 11 may set the average value between the average value of the degrees of matching with the evaluation item "comfortable/uncomfortable" and the average value of the degrees of matching with the evaluation item "like/dislike" as the degree of matching with the first classification item "comfort". The information on the degrees of matching with the respective first classification items thus calculated is associated with fragrances as the use purpose information and the obtained information is stored in the fragrance DB 20.

Referring is made once again to FIG. 4. In Step S12, the classification unit 11 acquires the smell quality information of each of the fragrances to be classified from the fragrance DB 20. The smell quality information is information generated in advance based on results of evaluating, by a number of examinees, the fragrance based on the smell quality as the evaluation axis. In this first embodiment, the smell quality information is information on the degree of matching of the fragrance with the second classification item. Just like the case in which an examinee evaluates a fragrance based on the purpose of use, the examinee smells a fragrance, and inputs, regarding the evaluation item of the smell quality that corresponds to the second classification item, a score indicating the degree of matching of this fragrance with this evaluation item, thereby evaluating the smell quality of the fragrance. The evaluation item here is, for example, "citrus", "tree" or "sweet", and is also referred to as a smell quality evaluation word. Then the classification unit 11 calculates the average of the degrees of matching with the evaluation item evaluated by a number of examinees, and sets this average value as the degree of matching with the second classification item. This processing may be performed before Step S11 or may be performed in parallel with Step S11.

In Step S13, the classification unit 11 classifies the fragrances to be classified into segments defined by two classification axes, that is, the purpose of use and the smell quality.

FIG. 6 is a diagram for describing processing of classifying the fragrances according to the first embodiment. FIG. 6 shows a classification table after the processing of classifying the fragrances but before processing of determining expression scents that will be described later. In FIG. 6, each segment indicates identification numbers (IDs) of fragrances that have been classified, and the degrees of matching M1, M2, or M3 of the respective fragrances to the first classification item that corresponds to this segment.

First, the classification unit 11 determines, for each of the fragrances to be classified, the second classification item of the fragrance based on the degree of matching with the second classification item and classifies the fragrances to be classified into row groups R1-R5. In FIG. 6, fragrances 110-112, fragrances 210-212, and fragrances 310-312 are classified into the row group R1. Further, the classification unit 11 determines, for each of the fragrances to be classified, the first classification item of the fragrance based on the degree of matching with each item on the first classification axis and classifies the fragrances to be classified into the column groups C1-C3. In FIG. 6, fragrances 110-112, fragrances 120-122, . . . , and fragrances 150-152 are classified into the column group C1. As a result, one or a plurality of fragrances are classified in each segment. Note that a known clustering method such as the K-means clustering method may be used as the classification processing into the row group or the column group described above.

Referring once again to FIG. 4, in Step S14, the classification unit 11 determines, for each segment, the expression scent from among the fragrances classified into this segment based on the degree of matching with the first classification item. In some embodiments, the expression scent is a fragrance that is highly robust and can thus be stably classified into the same segment even when the number of segments, the number of examinees, examinee attributes or the like in Steps S11-12 is slightly changed. However, each examinee has different likes and dislikes of fragrances, responses to the fragrances, and ways of determining the degrees of matching, and the problem is how to determine a fragrance that is highly robust. In the first embodiment, in order to appropriately set an expression scent, the classification unit 11 determines, for each segment, a fragrance whose degree of matching with the first classification item that corresponds to this segment is the highest among the fragrances classified into this segment to be the expression scent. In the table shown in FIG. 6, for example, the expression scent in the C1×R1 segment is the fragrance 110 whose degree of matching M1 with "comfort" is the highest (M1=9). The expression scent in the C1×R2 segment is the fragrance 121 whose degree of matching M1 with "comfort" is the highest (M1=8).

While the degree of matching with the first classification item is an average value of the degrees of matching with the evaluation item of the purpose of use that corresponds to the first classification item, the reason why the expression scent is a fragrance whose average value of the degrees of matching with the evaluation item is the highest (highest average fragrance) will be described below.

Figure 7:
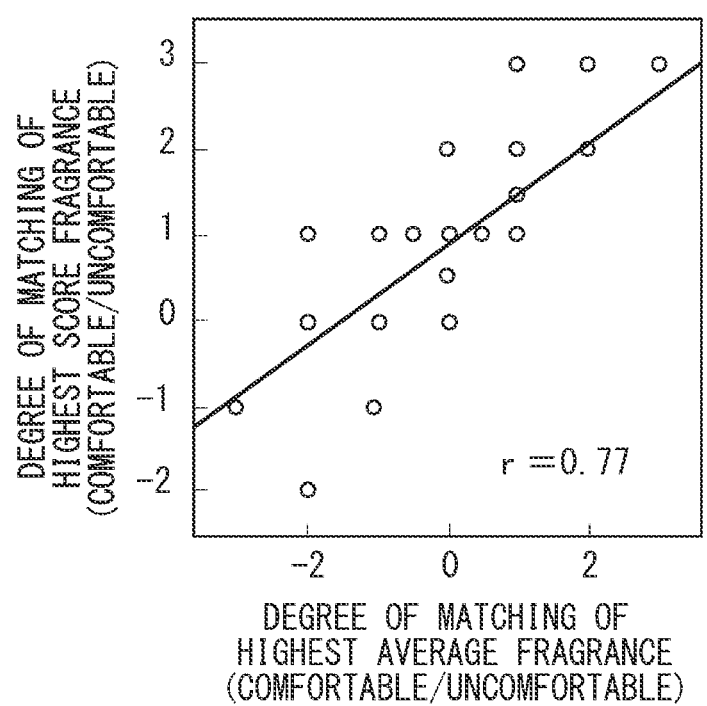
FIG. 7 is a diagram for describing processing of determining expression scents according to the first embodiment.
Figure 8:
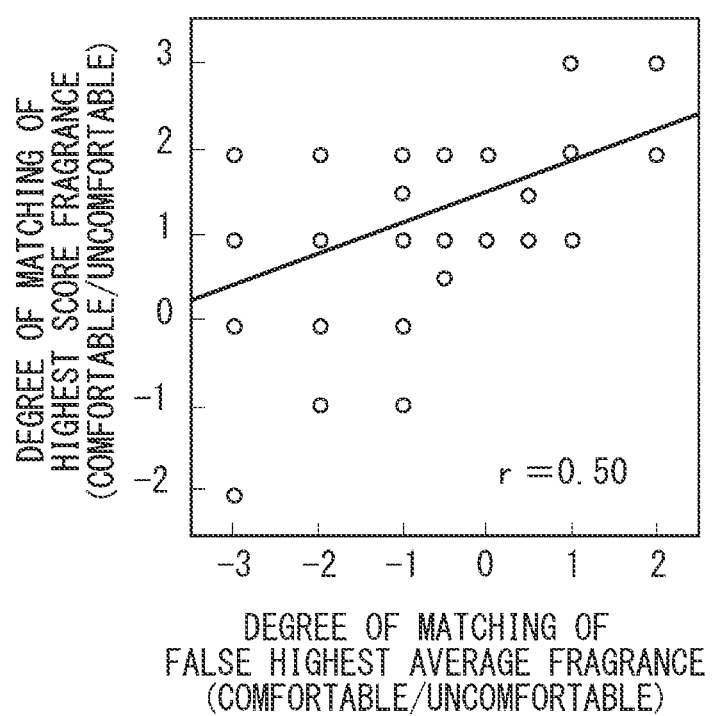
FIG. 8 is a diagram for describing the processing of determining the expression scents according to the first embodiment.
Figure 9:
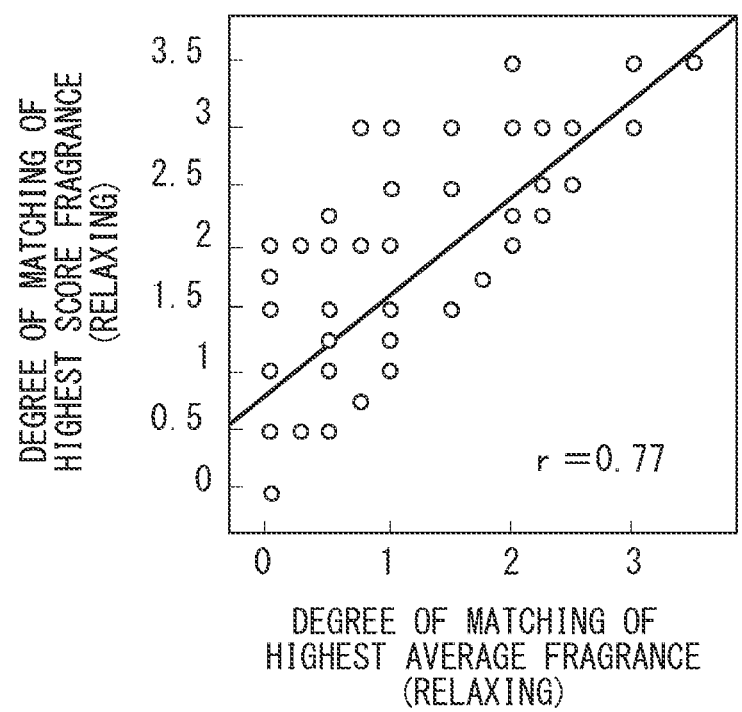
FIG. 9 is a diagram for describing the processing of determining the expression scents according to the first embodiment.
Figure 10:
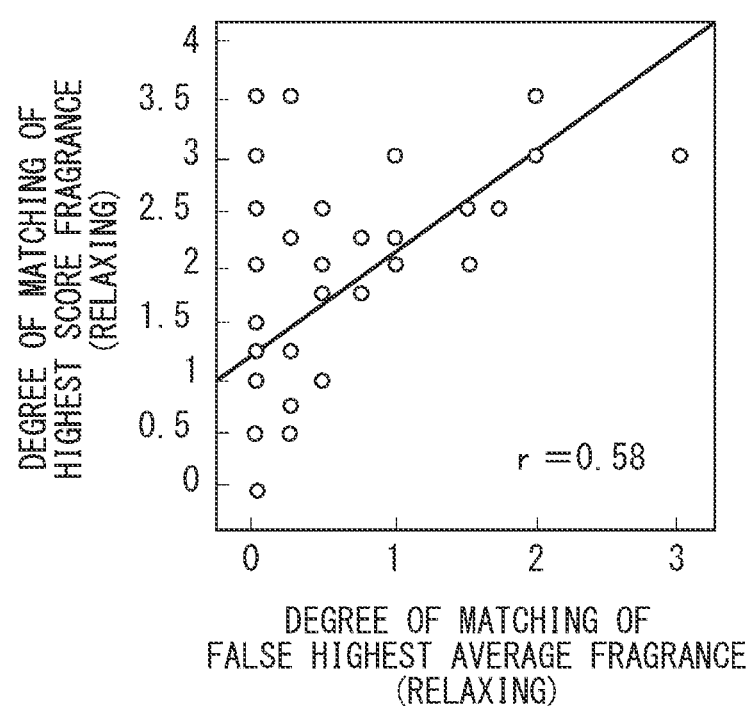
FIG. 10 is a diagram for describing the processing of determining the expression scents according to the first embodiment.
Figure 11:
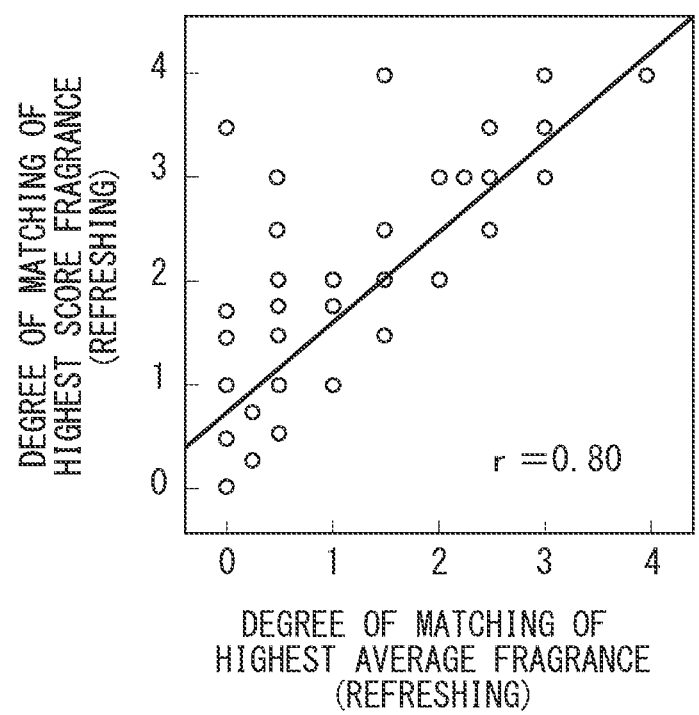
FIG. 11 is a diagram for describing the processing of determining the expression scents according to the first embodiment.
Figure 12:
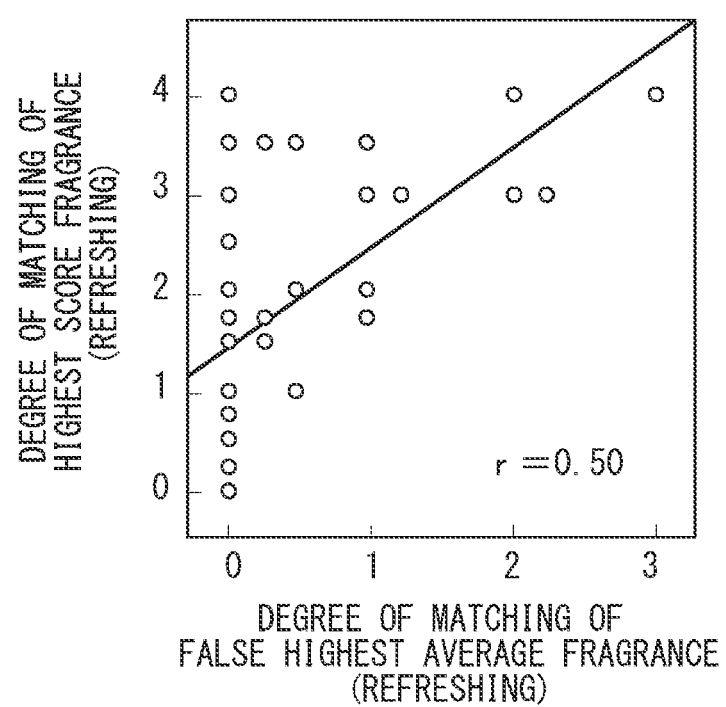
FIG. 12 is a diagram for describing the processing of determining the expression scents according to the first embodiment.

FIGS. 7-13 are diagrams for describing the processing of determining the expression scents according to the first embodiment. FIGS. 7-8, 9-10, and 11-12 respectively correspond to the evaluation items of emotion "comfortable/uncomfortable", "relaxing", and "refreshing". FIGS. 7, 9, and 11 each show a relation between the degree of matching evaluated by each examinee regarding the fragrance whose average value of the degrees of matching with the corresponding evaluation item of the emotion is the highest (highest average fragrance), and the degree of matching of the fragrance evaluated with the highest score by the examinee (highest score fragrance) among all the fragrances classified into one segment. FIGS. 8, 10, and 12 each show a relation between the degree of matching evaluated by each examinee regarding a fragrance that is not the highest average fragrance (false highest average fragrance) among all the fragrances classified into one segment and the degree of matching of the highest score fragrance.

As shown in FIGS. 7-12, regardless of whether a fragrance is the highest average fragrance or the false highest average fragrance, a positive correlation is observed between the degree of matching of the highest average fragrance or the false highest average fragrance and the degree of matching of the highest score fragrance. However, as shown in FIGS. 7, 9, and 11, correlation coefficients r between the degree of matching of the highest average fragrance and the degree of matching of the highest score fragrance with "comfortable/uncomfortable", "relaxing", and "refreshing" are respectively 0.77, 0.77, and 0.80, from which it can be said that there is a strong positive correlation therebetween. On the other hand, as shown in FIGS. 8, 10, and 12, correlation coefficients r between the degree of matching of the false highest average fragrance and the degree of matching of the highest score fragrance with "comfortable/uncomfortable", "relaxing", and "refreshing", are respectively 0.50, 0.58, and 0.50, which shows that the correlation of the false highest average fragrance with the highest score fragrance is weaker than the correlation of the highest average fragrance with highest score fragrance.

Figure 13:
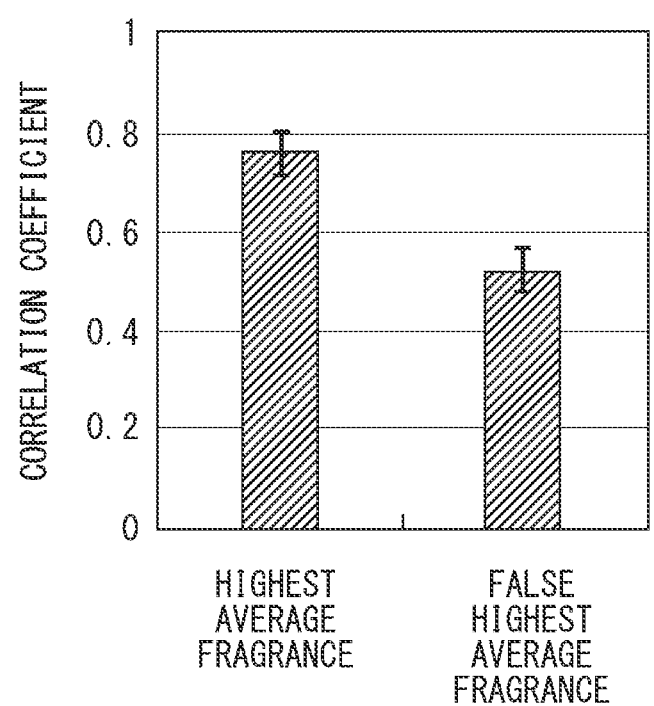
FIG. 13 is a diagram for describing the processing of determining the expression scents according to the first embodiment.

While FIG. 13 shows statistical values of the correlation coefficients of the highest average fragrance and the false highest average fragrance across a plurality of evaluation items, it is seen in this figure as well that the highest average fragrance has a stronger correlation with the highest score fragrance than the false highest average fragrance does.

As described above, the classification unit 11 determines the highest average fragrance, that is, a fragrance whose degree of matching with the first classification item corresponding to the segment is the highest as the expression scent, whereby the variety of the fragrances for evaluation are ensured more definitely, and appropriateness of the selection of fragrances for presentation at the time of subsequent operation is improved.

Referring is made once again to FIG. 4. In Step S15, the classification unit 11 generates the classification table T based on the expression scents that have been determined. The classification unit 11 may register, in each segment, besides information on the expression scents, information on the degrees of matching with the first classification item that corresponds to this segment. The classification unit 11 stores the generated classification table T in the fragrance DB 20 and ends the classification processing.

Figure 14:
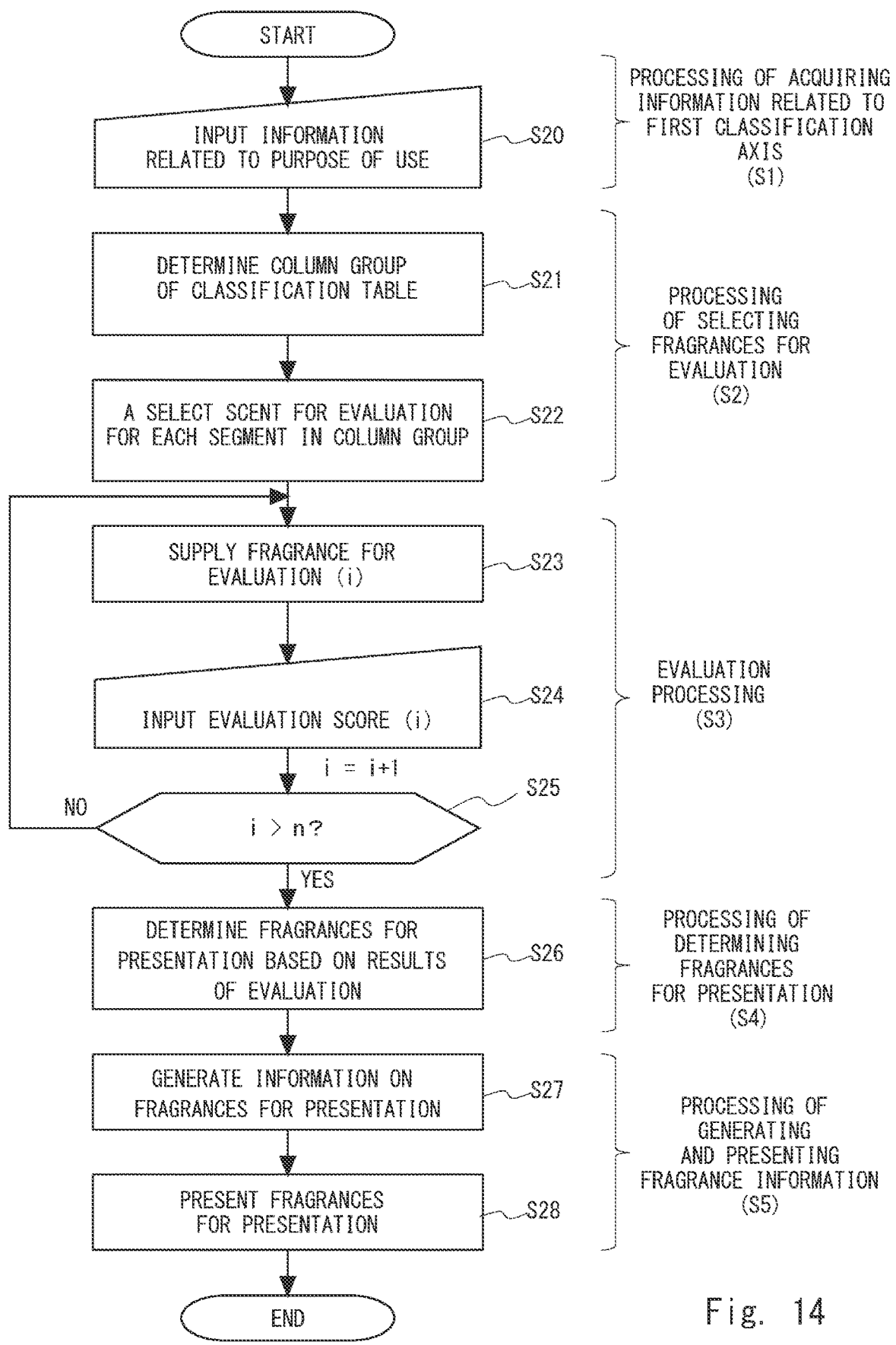
FIG. 14 is a flowchart showing a procedure for information processing when the information processing apparatus according to the first embodiment is operated.

FIG. 14 is a flowchart showing a procedure for the information processing when the information processing apparatus 10 according to the first embodiment is operated. The steps shown in FIG. 14 include processing of acquiring the information related to the first classification axis (Step S1), processing of selecting the fragrances for evaluation (Step S2), evaluation processing (Step S3), processing of determining the fragrance for presentation (Step S4), and processing of generating and presenting fragrance information (Step S5). In the first embodiment, Step S1 is formed of Step S20, Step S2 is formed of Steps S21 and S22, Step S3 is formed of Steps S23-S25, Step S4 is formed of Step S26, and Step S5 is formed of Steps S27 and S28. In the following, specific processing of Steps S20-S28 will be described.

First, in Step S20, the target person P inputs information related to the purpose of using a scent. The target person P may select, for example, the purpose of use from among "comfort", "relaxing", and "refreshing". Accordingly, the acquisition unit 12 of the information processing apparatus 10 acquires information related to the purpose of use by the target person P. The acquisition unit 12 supplies the acquired information to the selection unit 13.

Next, in Step S21, the selection unit 13 determines the first classification item based on the information related to the purpose of use, and the column group of the classification table T. Then, in Step S22, the selection unit 13 selects expression scents of the respective segments in the column group as the fragrances for evaluation using the classification table T. That is, the selection unit 13 selects expression scents of the respective segments that correspond to the determined first classification item and whose second classification items differ from each other as fragrances for evaluation. When, for example, the column group is C1, the selection unit 13 selects a total of five expression scents in the respective segments that are included in C1 and belong to R1-R5 as the fragrances for evaluation. Accordingly, in the following evaluation processing, it is possible to secure the variety of fragrances for evaluation and appropriately grasp the user's preference and physiological and/or psychological responses of the user while minimizing the number of fragrances evaluated by the target person P. Note that the selection unit 13 may select expression scents whose degrees of matching with the determined first classification item are equal to or larger than a predetermined threshold as the fragrances for evaluation. Accordingly, it is possible to reduce the number of fragrances evaluated by the target person P and further reduce the evaluation burden on the user. The selection unit 13 supplies information on the selected fragrances for evaluation to the evaluation unit 14.

Next, the processes shown in Steps S23-S25 are repeated for each of the fragrances for evaluation.

In Step S23, the evaluation unit 14 supplies the i (natural number)-th fragrance for evaluation via the supply device 40. Specifically, the fragrance for evaluation is adjusted in the supply device 40 in such a way that its concentration in the air at the position of the nose of the target person P is about "odor intensity 3: easily discernible odor" in the six grades odor intensity measurement method, and then this fragrance for evaluation is discharged or sprayed. The adjustment method may be, for example, a method of diluting the air containing fragrance components by mixing the air containing fragrance components with odorless air (air that does not contain fragrance components) at a predetermined ratio. Then the target person P smells the supplied fragrance for evaluation.

In Step S24, the target person P inputs the evaluation score for the i-th fragrance for evaluation that has been supplied. The evaluation score is one example of evaluation information indicating the results of the evaluation made by the target person P. Accordingly, the evaluation unit 14 of the information processing apparatus 10 acquires the evaluation score of the fragrance for evaluation. The evaluation by the target person P may be performed using an evaluation sheet similar to the evaluation sheet A shown in FIG. 5. Therefore, the evaluation score may be an index similar to the degree of matching with the evaluation item that corresponds to the first classification item used in the classification processing. However, the evaluation score is not limited thereto. Then the evaluation unit 14 increments the value of i. In Step S25, the evaluation unit 14 determines whether i has exceeded the total number n of fragrances for evaluation, that is, whether all the fragrances for evaluation have been evaluated. When not all the fragrances for evaluation have been evaluated (NO in Step S25), the evaluation unit 14 returns the process to Step S23. On the other hand, when all the fragrances for evaluation have been evaluated (YES in Step S25), the evaluation unit 14 proceeds the processing to Step S26.

In Step S26, the evaluation unit 14 determines the fragrances for presentation based on the results of the evaluation. In the first embodiment, the evaluation unit 14 determines fragrances for evaluation having evaluation scores equal to or higher than a predetermined threshold to be the fragrances for presentation. Alternatively, the evaluation unit 14 may determine a fragrance for evaluation having the highest evaluation score or fragrances for evaluation having high (e.g., the three highest) evaluation scores to be the fragrances for presentation. The evaluation unit 14 supplies the information on the fragrances for presentation to the generation unit 15.

In Step S27, the generation unit 15 generates information on the fragrances for presentation. Then, in Step S28, the generation unit 15 causes the supply device 40 to supply the fragrances for presentation. Further, the generation unit 15 causes the display input device 30 to display the information on the fragrances for presentation. In addition, the generation unit 15 may cause the display input device 30 to display the results of analyzing the preference and physiological and/or psychological responses of the target person P based on the evaluation score. Accordingly, the target person P will likely to be convinced that the presented fragrance is suitable for the target person P and is likely to have the impression that it is a special scent only for him/her. Then the generation unit 15 ends the process.

While the number of classification tables T is one in the first embodiment, different classification tables T may be generated depending on the attributes such as the sex, the age group, or the classification of occupation, or usage conditions such as the season, the time zone, or the place and may be used in operation. In this case, in Step S20, the acquisition unit 12 may accept and acquire input of attribute information of the target person P or usage condition information from the target person P via the display input device 30. Then, prior to Step S21, the selection unit 13 may select the classification table T to be used based on the attribute information or the usage condition information.

As described above, according to the first embodiment, the information processing apparatus 10 narrows down the fragrances based on objective input information of the target person P regarding the first classification item and narrows down the fragrances based on the sensitivity of the target person P regarding the second classification item. The target person P only needs to actually evaluate fragrances narrowed down to a small number based on the first classification item, whereby the number of evaluations is reduced and the evaluation burden is reduced. Since the fragrances narrowed down to a small number based on the first classification item are fragrances whose second classification items differ from each other, variety is ensured. Therefore, the information processing apparatus 10 is able to appropriately select fragrances for presentation in accordance with the individual differences in the preferences and responses of the target person P from among various fragrances, and present the selected fragrances to the target person P.

Since the fragrances for evaluation that the target person P actually evaluates are expression scents that represent the respective segments, the information processing apparatus 10 is able to ensure the variety of fragrances for evaluation, more appropriately select fragrances for presentation, and present the selected fragrances to the target person P.

Second Embodiment

Figure 15:
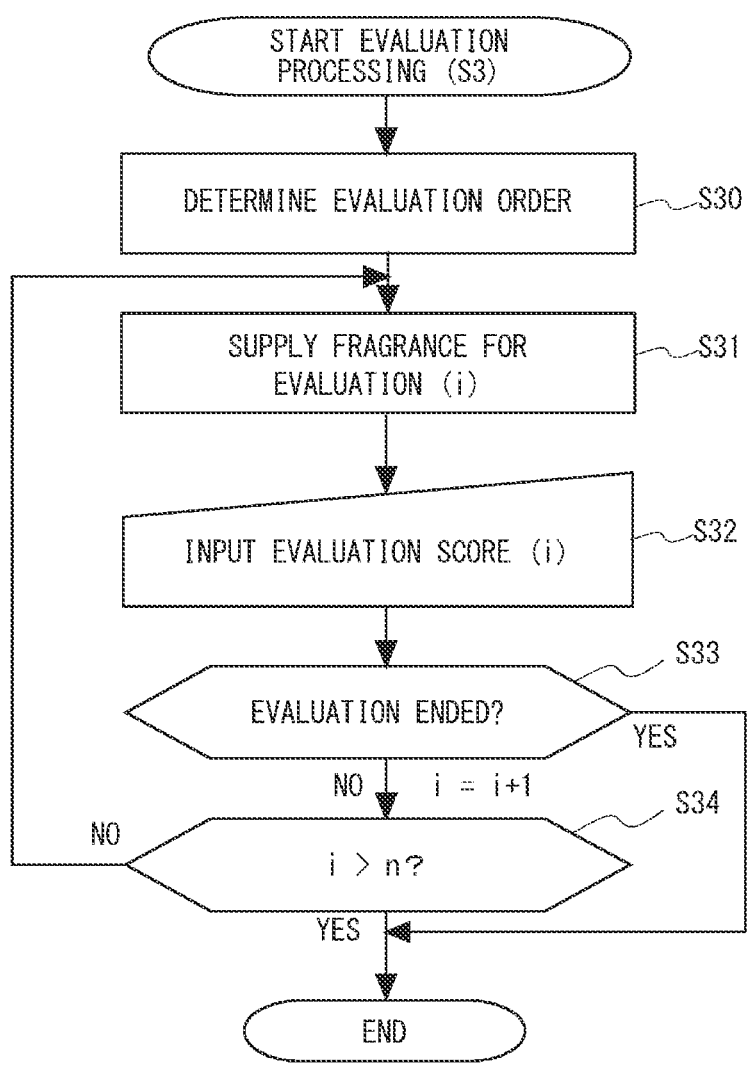
FIG. 15 is a flowchart showing a procedure for evaluation processing according to a second embodiment.

Referring next to FIG. 15, a second embodiment will be described. An information processing apparatus 10 according to the second embodiment is basically similar to the information processing apparatus 10 according to the first embodiment. However, the procedure for the evaluation processing by the evaluation unit 14 (Step S3 in FIG. 14) in the second embodiment is different from that in the first embodiment.

FIG. 15 is a flowchart showing a procedure for evaluation processing according to the second embodiment.

First, in Step S30, the evaluation unit 14 determines an evaluation order of the fragrances for evaluation by the target person P based on the degrees of matching with the first classification item determined in the selection processing (Step S2 in FIG. 14). Specifically, the evaluation unit 14 allows the target person P to evaluate fragrances for evaluation from the fragrance for evaluation whose degree of matching with the first classification item is the highest in order. When, for example, the first classification item is "comfort", the evaluation unit 14 causes the target person P to evaluate the fragrances from the one whose degree of matching M1 is the highest in the column group C1, that is, in the order of R1→R2→R4→R3→R5 (see FIG. 6). Next, the processing shown in Steps S31-34 is repeated based on the evaluation order.

In Step S31, similar to Step S23, the evaluation unit 14 supplies the i (natural number)-th fragrance for evaluation via the supply device 40. The target person P smells the supplied fragrance for evaluation. In Step S32, like in Step S24, the target person P inputs an evaluation score for the i-th fragrance for evaluation that has been supplied. Next, in Step S33, the evaluation unit 14 determines whether to end (interrupt) evaluation of fragrances for evaluation by the target person P. When, for example, the evaluation score is smaller than a predetermined threshold or when the evaluation score is lower than the evaluation score of the fragrance for evaluation that has been input just before this evaluation score is input by a predetermined threshold or more, the evaluation unit 14 determines that the evaluation will be interrupted. When the evaluation is not interrupted (NO in Step S33), the evaluation unit 14 increments the value of i and determines whether all the fragrances for evaluation have been evaluated (Step S34). Then, when not all the fragrances for evaluation have been evaluated (NO in Step S34), the evaluation unit 14 returns the process to Step S31. When all the fragrances for evaluation have already been evaluated (YES in Step S34), the process is ended. On the other hand, when the evaluation is interrupted (YES in Step S33), the evaluation unit 14 immediately ends the process.

The evaluation unit 14 determines, in the subsequent determination processing (Step S4), the fragrances for presentation based on the results of evaluating the fragrances for evaluation.

As described above, the evaluation unit 14 of the information processing apparatus 10 according to the second embodiment causes the target person P to input evaluation scores of fragrances for evaluation from the one whose degree of matching with the first classification item determined based on the information related to the first classification axis is the highest in order. Further, when the input evaluation score is low or the evaluation score has been significantly reduced from the evaluation score of the fragrance for evaluation that has been input just before this evaluation score is input, the evaluation unit 14 interrupts acceptance of the input of the evaluation scores. Accordingly, the evaluation by the target person P is ended early, whereby the evaluation burden on the target person P can be further reduced.

In addition thereto, the evaluation unit 14 may analyze the preference or physiological and/or psychological responses of the target person P based on the degrees of matching with the first classification item and evaluation scores of the target person P at a timing when the evaluation of some fragrances for evaluation by the target person P is ended, and change the order of the fragrances for evaluation that will be evaluated thereafter. For example, at a timing when the fragrances for evaluation that belong to R4 are evaluated, the evaluation unit 14 may change the evaluation order of the remaining fragrances for evaluation to R5→R3 while the original evaluation order is R1→R2→R4→R3→R5. Accordingly, by ending the evaluation by the target person P early, the evaluation burden on the target person P can be further reduced.

In the aforementioned description, the evaluation unit 14 determines the evaluation order based on the degrees of matching with the first classification item that has been determined. In addition thereto or instead of the above, the evaluation unit 14 may determine the evaluation order based on the attribute information of the target person P or the usage condition information.

Third Embodiment

Figure 16:
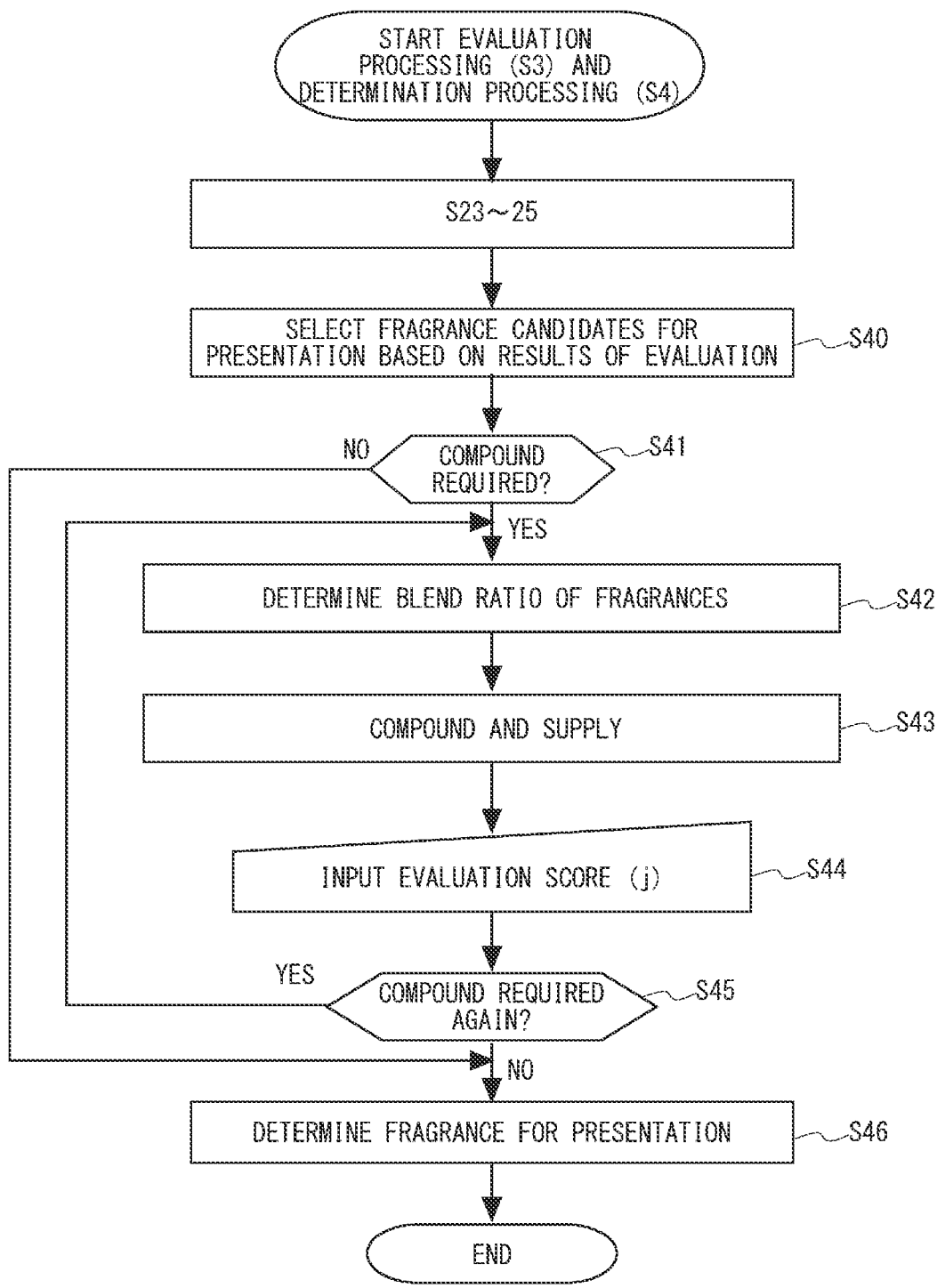
FIG. 16 is a flowchart showing procedures for evaluation processing and determination processing according to a third embodiment.

Referring next to FIG. 16, a third embodiment will be described. An information processing apparatus 10 according to the third embodiment is basically similar to the information processing apparatus 10 according to the first embodiment. In the third embodiment, procedures for the evaluation processing and the determination processing (Steps S3 and S4 in FIG. 14) by the evaluation unit 14 are different from those in the first embodiment.

FIG. 16 is a flowchart showing procedures for evaluation processing and determination processing according to the third embodiment.

First, after the processing in Steps S23-S25, in Step S40, the evaluation unit 14 selects fragrance candidates for presentation based on the results of the evaluation. The method of selecting the fragrance candidates for presentation may be similar to the method of selecting the fragrances for presentation in Step S26. For example, the fragrance candidates for presentation are fragrances for evaluation having evaluation scores equal to or higher than a predetermined threshold among the fragrances for evaluation. The number of kinds of the fragrance candidates for presentation may be between two and five. Then, in Step S41, the evaluation unit 14 determines whether it is required to compound fragrance candidates for presentation and generate fragrances for presentation. A case in which it is required to compound fragrance candidates for presentation and generate fragrances for presentation is a case in which there are a plurality of fragrance candidates for presentation, a case in which the target person P prefers a more highly evaluated fragrance, or a case in which the target person P desires to make changes to scents. When it is required to compound fragrance candidates for presentation (YES in Step S41), the evaluation unit 14 proceeds the processing to Step S42. Otherwise (NO in Step S41), the evaluation unit 14 proceeds the processing to Step S46.

In Step S42, the evaluation unit 14 determines the blend ratio of fragrance candidates for presentation. The evaluation unit 14 calculates the blend ratio by making the ratio of evaluation scores correspond to the sensory intensity ratio. According to the Weber-Fechner law, when the sensory intensity is denoted by Y, the stimulus amount is denoted by X, and stimulus-specific constants are denoted by a and b, the sensory intensity is expressed by a logarithmic function expression $Y = a \log X + b$. When, for example, the first classification item is "relaxing" and the evaluation scores of the respective fragrances A, B, and C are respectively 4, 3, and 2, its blend ratio is expressed as $e^4:e^3:e^2 7:3:1$. Accordingly, the evaluation unit 14 calculates the blend ratio in such a way that this blend ratio is a ratio of the power where the base is e and the exponent is the evaluation score.

In Step S43, the evaluation unit 14 transmits information on the fragrances to be blended and information on the blend ratio to the supply device 40, and causes the supply device 40 to compound the fragrances based on these information items and supply the compounded fragrance to the target person P.

In Step S44, the target person P inputs an evaluation score for the compounded fragrance. Accordingly, the evaluation unit 14 of the information processing apparatus 10 acquires the evaluation score of the compounded fragrance.

Next, in Step S45, the evaluation unit 14 determines whether or not a fragrance needs to be compounded again. When, for example, the evaluation score of the compounded fragrance is lower than the highest evaluation score of the fragrance candidates for presentation, the evaluation unit 14 may determine that a fragrance needs to be compounded again. Even in this case, when the number of evaluations by the target person P exceeds a predetermined threshold, the evaluation unit 14 may determine that there is no need to compound fragrances again. When a fragrance needs to be compounded again (YES in Step S45), the evaluation unit 14 returns the process to Step S42, and changes the blend ratio based on the evaluation score of the compounded fragrance and the evaluation score of fragrance candidate for presentation.

On the other hand, when there is no need to compound fragrances again (NO in Step S45), the evaluation unit 14 proceeds the processing to Step S46.

In Step S46, the evaluation unit 14 determines the compounded fragrance or the fragrance candidates for presentation as the fragrances for presentation. In this case, the evaluation unit 14 may determine which fragrances should be presented as fragrances for presentation based on the evaluation score of the compounded fragrance or the evaluation scores of the fragrance candidates for presentation. Then the evaluation unit 14 ends the processing.

As described above, according to the third embodiment, the evaluation unit 14 of the information processing apparatus 10 determines the fragrances obtained by blending the fragrance candidates for presentation in accordance with the evaluation score to be the fragrances for presentation. Therefore, the information processing apparatus 10 is able to present scents that are more appropriate for the target person P.

When the evaluation unit 14 causes the supply device 40 to supply the compounded fragrance to the target person P in Step S43, the evaluation unit 14 may cause the display input device 30 to display information on the compounded fragrance. Then the evaluation unit 14 may cause the display input device 30 to display results of analyzing the preference and physiological and/or psychological responses of the target person P based on the results of the evaluation by the target person P.

The evaluation unit 14 may cause, for example, the display input device 30 to display the main fragrance based on the results of the analysis to let the target person P know what scent is likely to bring the target person P to be a desired state.

Further, for example, the evaluation unit 14 causes the display input device 30 to display information on a fragrance that is recommended to be added to the main fragrance based on the results of the analysis to notify the target person P of this information. As one example, when the purpose of use is "relaxing", the display input device 30 may display a comment such as "'You will be "relaxed" with a "woody scent (tree scent)". For a "relaxing holiday", add a scent of "lavender" and "you may feel like you are staying at a resort'". The parts in parentheses " " may be changed depending on the results of the evaluation. The display input device 30 may further display "recommendation this time: frankincense+lavender". When the purpose of use is to "refresh", the display input device 30 may display a comment such as "'You will feel "refreshing" with "a citrus scent". "On the morning of an important meeting", add a scent of "mint" and you will "feel energized."'" Then the display input device 30 may further display "recommendation this time: grapefruit+peppermint".

Accordingly, the target person P will likely to be convinced that the compounded fragrance that will be supplied is appropriate and is likely to have the impression that it is a special scent only for him/her.

Fourth Embodiment

Figure 17:
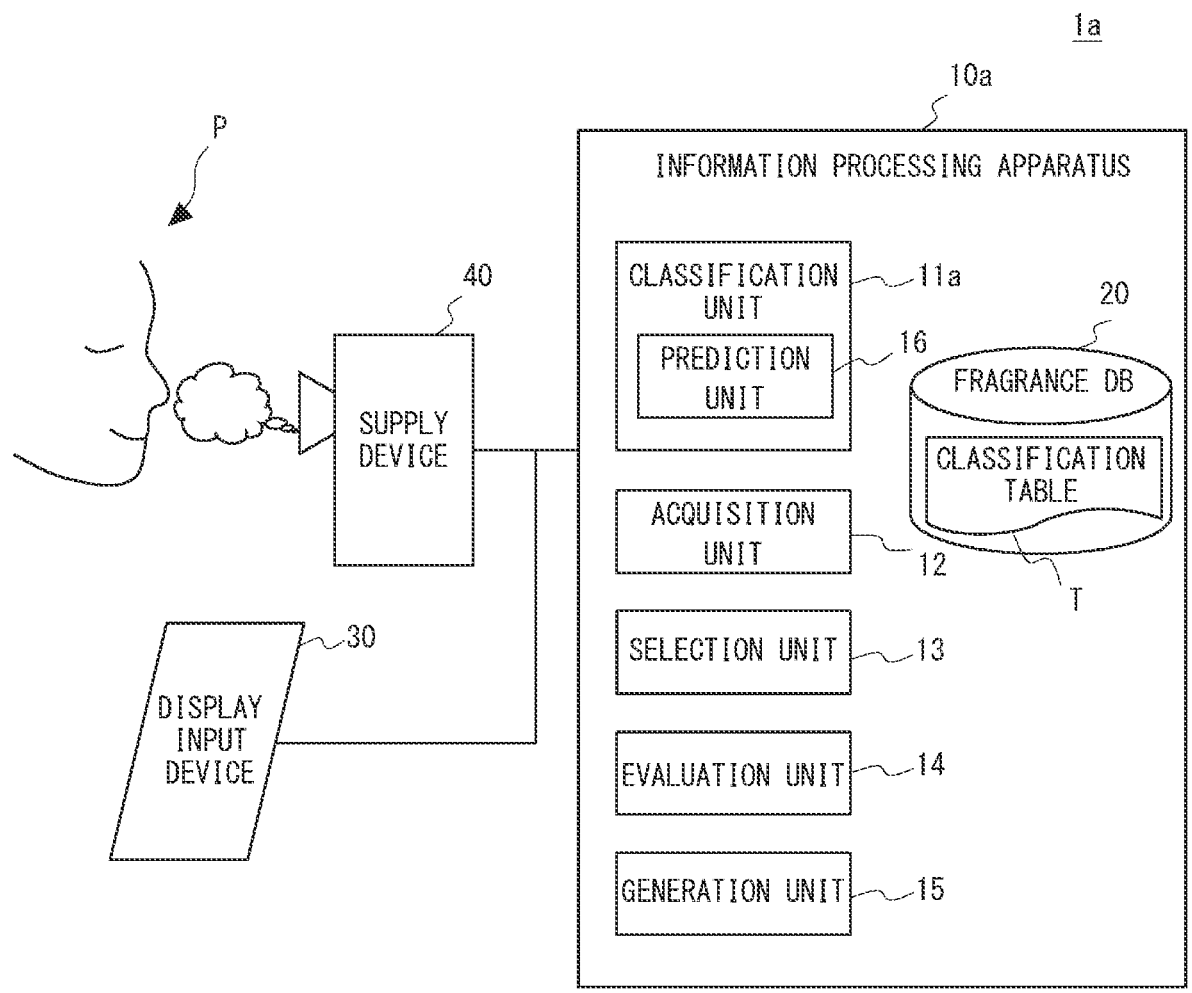
FIG. 17 is a schematic configuration diagram of a scent presentation system according to a fourth embodiment.
Figure 18:
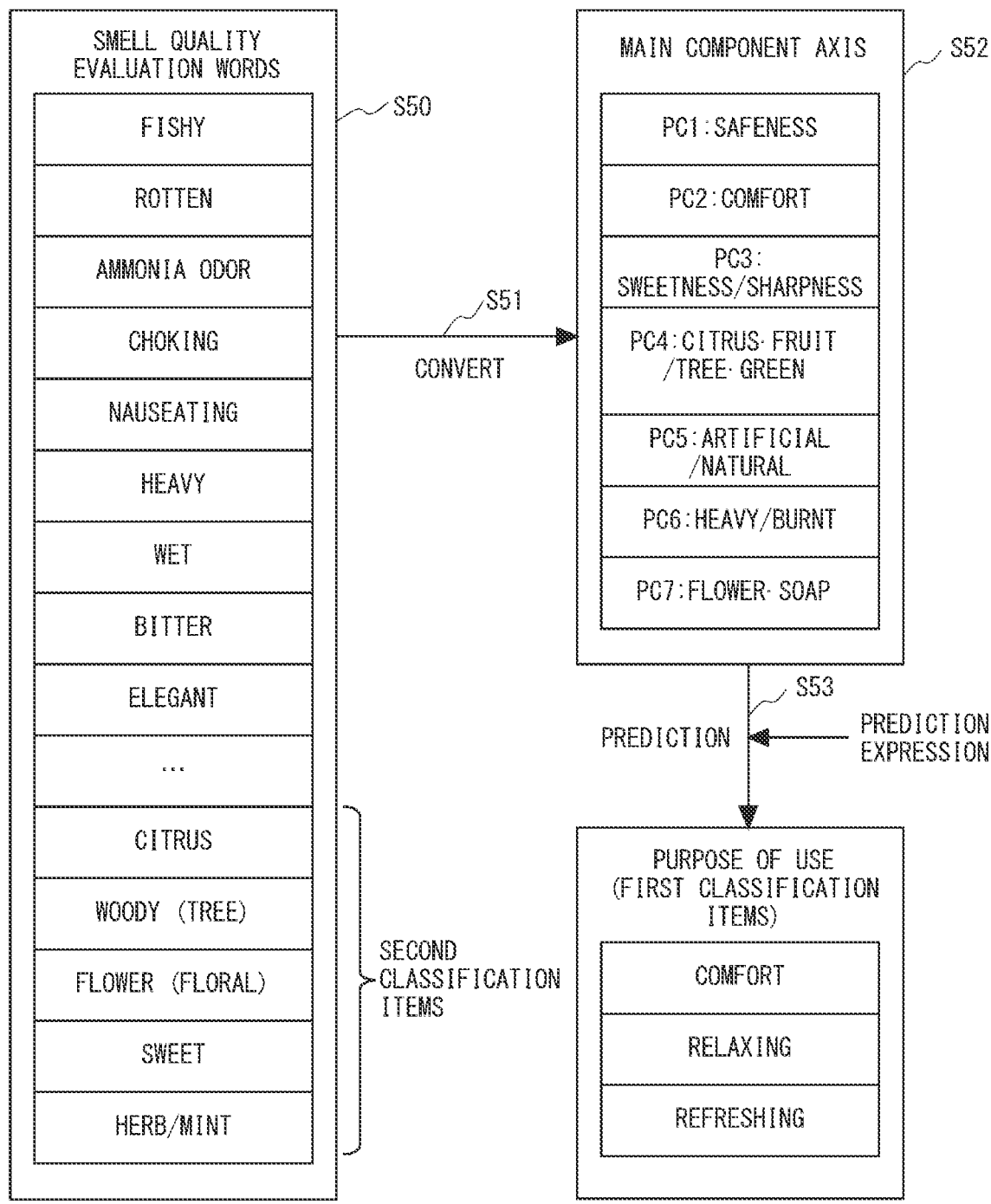
FIG. 18 is a diagram for describing prediction processing according to the fourth embodiment.
Figure 19:
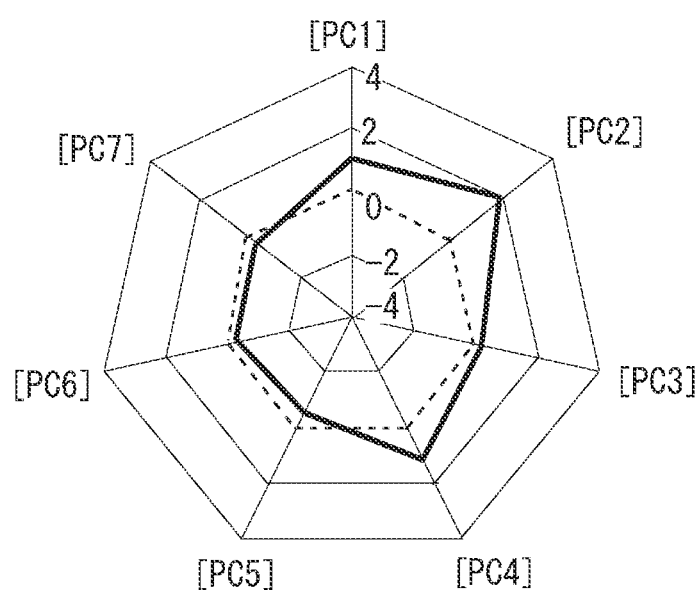
FIG. 19 is a diagram showing one example of a radar chart of principal component scores of fragrances according to the fourth embodiment.

With reference next to FIGS. 17-19, a fourth embodiment will be described. In the first embodiment, the use purpose information used for the classification processing is generated based on results of evaluating, by a number of examinees, fragrances based on the purpose of use as the evaluation axis. However, in the fourth embodiment, the use purpose information used for the classification processing is generated based on results of evaluating, by a number of examinees, fragrances based on the smell quality as the evaluation axis.

FIG. 17 is a schematic configuration diagram of a scent presentation system 1a according to the fourth embodiment. While the scent presentation system 1a according to the fourth embodiment basically has a configuration and a function similar to those of the scent presentation system 1 according to the first embodiment, they are different from each other in that the scent presentation system 1a includes an information processing apparatus 10a in place of the information processing apparatus 10.

While the information processing apparatus 10a basically has a configuration and a function similar to those of the information processing apparatus 10, the information processing apparatus 10a includes a classification unit 11a in place of the classification unit 11.

The classification unit 11a includes, besides the functions of the classification unit 11, a prediction unit 16.

The prediction unit 16 predicts a degree of matching with the first classification item from degrees of matching with a plurality of kinds of smell quality evaluation words. The plurality of kinds of smell quality evaluation words, which are evaluation words related to the smell quality, may at least include the second classification items ("citrus", "tree", "sweet", etc.) In this fourth embodiment, the smell quality evaluation words include 39 items, and include, for example, besides the second classification items, "fishy", "choking", "elegant" and the like. Then the classification unit 11 executes classification processing using the degree of matching with the first classification item predicted by the prediction unit 16.

FIG. 18 is a diagram for describing prediction processing according to the fourth embodiment.

First, a number of examinees evaluate, for each of the fragrances to be classified, the fragrance and inputs the degrees of matching with the smell quality evaluation words shown in FIG. 18. The information on the degrees of matching with the smell quality evaluation words is supplied to the fragrance DB 20. The prediction unit 16 acquires, for each of the fragrances to be classified, information on the degrees of matching with the smell quality evaluation words from the fragrance DB 20 (Step S50).

Then the prediction unit 16 converts the degrees of matching with the smell quality evaluation words into principal component scores of each main component axis with fewer number of dimensions (Step S51). The principal component scores, which are expressed by linear combination of the degrees of matching with the respective smell quality evaluation words, are calculated using the degrees of matching with the respective smell quality evaluation words.

The main component axis is calculated prior to the prediction processing. The main component axis is calculated in advance by performing a principal component analysis on the degrees of matching with the smell quality evaluation words evaluated by preliminary examinees regarding various fragrances (e.g., 93 kinds).

In this fourth embodiment, the main component axis is divided into first to seven main component axes (PC1-PC7) depending on contribution rates. As one example, the first to seventh component axes include safeness (PC1), comfort (PC2), sweetness/sharpness (PC3), citrus•fruit/tree•green (PC4), artificial/natural (PC5), heavy/burnt (PC6), and flower•soap (PC7). In this way, by converting the degrees of matching of the smell quality evaluation words into principal component scores of each main component axis, the number of dimensions can be significantly reduced while maintaining the features on smell quality.

Then the prediction unit 16 calculates, for each fragrance, an average value of the principal component scores of each main component axis among examinees (Step S52). Specifically, the prediction unit 16 generates, for each fragrance, a radar chart of average values of the principal component scores as shown in FIG. 19. FIG. 19 shows one example of the radar chart of the principal component scores of the fragrance. The features of the respective fragrances are expressed in a heptagonal radar chart in accordance with the average values of the principal component scores.

Next, the prediction unit 16 predicts the degrees of matching with the respective first classification items from the principal component scores of the main component axis using a prediction expression (Step S53). The prediction expression is also generated prior to prediction processing. The prediction expression is generated using the degrees of matching with the smell quality evaluation words evaluated by the preliminary examinees for various fragrances (e.g., 93 kinds) and the degree of matching with the first classification item evaluated by the preliminary examinees for the same fragrances. For example, the prediction expression is derived by a multiple regression analysis using a stepwise method with the degrees of matching with the smell quality evaluation words as explanatory variables and the degrees of matching with the first classification items as objective variables.

Prediction expressions of the degrees of matching with the first classification items "comfort", "relaxing", and "refreshing" are expressed, for example, as shown below.

$$[\text{Degree of matching with comfort}] = 0.13 + 0.83 \times [PC2] + 0.32 \times [PC1] - 0.17 \times [PC6] + 0.13 \times [PC3] + 0.07 \times [PC5] + 0.06 \times [PC7]$$

$$[\text{Degree of matching with relaxing}] = 0.60 + 0.57 \times [PC2] - 0.18 \times [PC4] + 0.07 \times [PC1] + 0.06 \times [PC6] + 0.05 \times [PC7] + 0.03 \times [PC3]$$

$$[\text{Degree of matching with refreshing}] = 0.68 + 0.72 \times [PC2] - 0.24 \times [PC3] + 0.09 \times [PC1] + 0.07 \times [PC4] - 0.07 \times [PC5]$$

The symbols [PC1], [PC2], . . . and [PC7] are respectively the principal component scores of PC1-PC7. The coefficients shown before the principal component scores are standard partial regression coefficients.

Different prediction expressions may be generated depending on user attributes or usage conditions and may be used to predict the degrees of matching with the respective first classification items.

Then the classification unit 11 performs classification processing into the column groups C1-C3 using information on the degrees of matching with the respective first classification items that have been predicted as the use purpose information. In the first embodiment, the classification unit 11 performs classification processing into the row groups R1-R5 using information on the degrees of matching with the respective second classification items that correspond to the smell quality. It is known, however, that, for fragrances with smell qualities similar to each other, the radar chart shown in FIG. 19 described above has shapes similar to each other. In the fourth embodiment, the classification unit 11 may perform classification processing into the row groups R1-R5 based on the shape of the radar chart shown in FIG. 19 described above.

As described above, the prediction unit 16 predicts the use purpose information using results of evaluating, by an examinee, the smell quality as the evaluation axis, which eliminates the trouble of evaluating, by the examinee, the fragrance based on the purpose of use as the evaluation axis.

Fifth Embodiment

Figure 20:
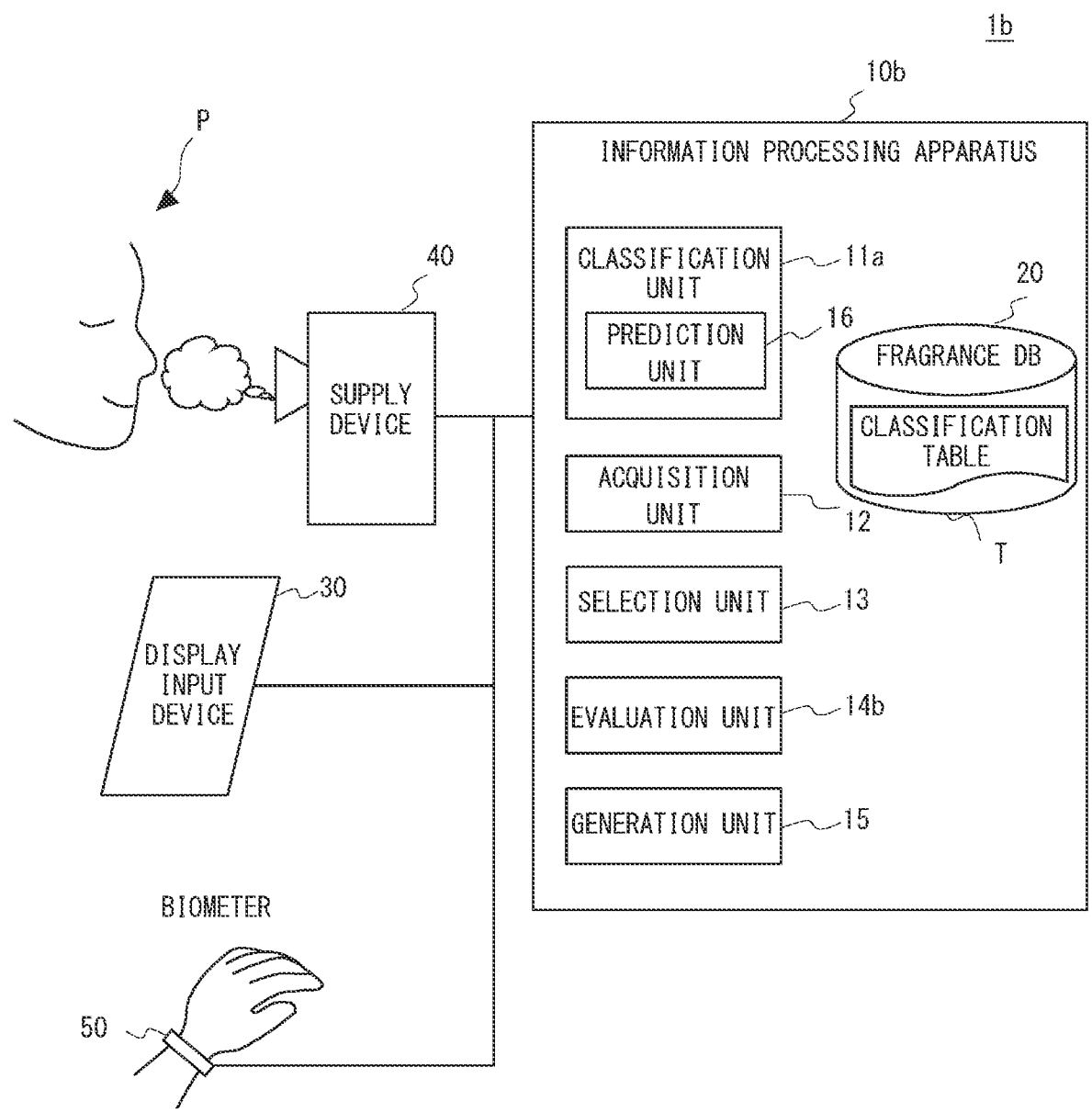
FIG. 20 is a schematic configuration diagram of a scent presentation system according to a fifth embodiment.

With reference next to FIG. 20, a fifth embodiment will be described. The fifth embodiment acquires evaluation information based on biological information instead of accepting, by an information processing apparatus, input of evaluation information (evaluation scores) from the target person P in evaluation processing.

FIG. 20 is a schematic configuration diagram of a scent presentation system 1b according to the fifth embodiment. While the scent presentation system 1b according to the fifth embodiment basically has a configuration and a function similar to those of the scent presentation system 1a according to the fourth embodiment, they are different from each other in that the scent presentation system 1b according to the fifth embodiment includes a biometer 50 and an information processing apparatus 10b in place of the information processing apparatus 10a.

The biometer 50 is a measuring instrument that measures and monitors biological information of the target person P. The biological information is information regarding the pulse or the heartbeat (e.g., information on the heart rate or heart rate intervals). The biometer 50 is, for example, a pulse sensor or a heart rate sensor. While shown in FIG. 20 is a biometer 50 of a contact type, it may be of a non-contact type. The biometer 50 transmits the biological information to the information processing apparatus 10b in accordance with measurement of the biological information of the target person P.

While the information processing apparatus 10b basically has a configuration and a function similar to those of the information processing apparatus 10a, they are different from each other in that the information processing apparatus 10b includes an evaluation unit 14b in place of the evaluation unit 14.

While the evaluation unit 14b basically has a configuration and a function similar to those of the evaluation unit 14, they are different from each other in that the evaluation unit 14b is connected to the biometer 50 and estimates evaluation scores of scents from the received biological information of the target person P. The evaluation unit 14b estimates, for example, that the higher the heart rate of the target person P is, the lower the evaluation score is. The evaluation unit 14b also estimates that the shorter the heart rate intervals of the target person P is, the lower the evaluation score is. Accordingly, the evaluation unit 14b acquires evaluation scores of scents from the biological information of the target person P, and uses the acquired evaluation scores in the subsequent evaluation processing.

The biological information may be information regarding the line of sight. In this case, the biometer 50 may be a camera that captures images of the face of the target person P and transmits image data obtained by capturing the face of the target person P to the evaluation unit 14b. Then the evaluation unit 14b may acquire the information regarding the line of sight by executing image processing based on the image data received from the biometer 50. Then the evaluation unit 14b may estimate that the evaluation score is low when a visual line movement amount or when the frequency of the movement of the visual line is large.

As described above, according to the fifth embodiment, the information processing apparatus 10b is able to perform evaluation processing based on the biological information automatically measured even when the target person P does not input evaluation scores, whereby the evaluation burden on the target person P can be reduced. Since the biological information includes unconscious physiological reactions of the target person P, the information processing apparatus 10b is able to improve the accuracy of the evaluation by using the biological information and more appropriately select fragrances for presentation. Note that the information processing apparatus 10b may use the biological information in combination with evaluation scores input by the target person P. The evaluation unit 14b may use, for example, evaluation scores estimated based on the biological information for the evaluation processing as unconscious emotion evaluation scores and use evaluation scores input by the target person P for the evaluation processing as evaluation scores in a conscious state. Alternatively, the evaluation unit 14b may correct the evaluation scores input by the target person P based on the biological information.

Note that the present disclosure is not limited to the above embodiments and may be changed as appropriate without departing from the spirit of the present disclosure.

For example, in the first to fifth embodiments, the first classification axis is related to the purpose of using a fragrance and the second classification axis relates to the smell quality of the fragrance. However, these are merely examples, and the classification axes may be related to examinee's attributes or usage conditions.

Further, in the first to fifth embodiments, it is assumed that one expression scent is registered in one segment in order to minimize the evaluation burden by the target person. However, this is merely one example and the number of kinds of the expression scents registered in one segment may be set as appropriate depending on conditions. The method of setting the number of kinds of the expression scents in one segment may be similar to the method of setting the number of row groups. In this case, in Step S14, the classification unit 11 may determine, for each segment, some of the fragrances classified into this segment whose degrees of matching with the first classification item that corresponds to this segment are high to be the expression scents.

While the present disclosure has been described as a hardware configuration in the aforementioned embodiments, the present disclosure is not limited thereto. The present disclosure may implement various kinds of processing related to the information processing method by causing a processor to execute a computer program.

In the aforementioned examples, the program includes instructions (or software codes) that, when loaded into a computer, cause the computer to perform one or more of the functions described in the embodiments. The program may be stored in a non-transitory computer readable medium or a tangible storage medium. By way of example, and not a limitation, non-transitory computer readable media or tangible storage media can include a random-access memory (RAM), a read-only memory (ROM), a flash memory, a solid-state drive (SSD) or other types of memory technologies, a CD-ROM, a digital versatile disc (DVD), a Blu-ray (registered trademark) disc or other types of optical disc storage, and magnetic cassettes, magnetic tape, magnetic disk storage or other types of magnetic storage devices. The program may be transmitted on a transitory computer readable medium or a communication medium. By way of example, and not a limitation, transitory computer readable media or communication media can include electrical, optical, acoustical, or other forms of propagated signals.

In the aforementioned embodiments, the computer is formed of a computer system including a personal computer or a word processor. However, this is merely one example, and the computer may be formed of a server of a Local Area Network (LAN), a host of computer (personal computer) communication, a computer system connected on the Internet or the like. Further, functions may be distributed to the respective devices on the network and the entire network may form the computer.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. An information processing system for presenting a scent to a target person comprising:
   at least one memory storing instructions, and at least one processor configured to execute the instructions to:
classify a plurality of fragrances into segments defined corresponding to a combination of one of first classification items on a first classification axis with one of second classification items on a second classification axis;
accept input of information related to the first classification axis from the target person;
determine one of the first classification items based on the information related to the first classification axis and select at least one fragrance for evaluation from each of segments that correspond to the first classification item and whose second classification items differ from each other;
acquire, for each of the fragrances for evaluation that have been selected, evaluation information of a scent from the target person; and
generate information on a fragrance for presentation based on the evaluation information, wherein:
the evaluation information includes evaluation scores,
the at least one processor executes the instructions to cause the target person to input evaluation scores of fragrances for evaluation from the fragrance for evaluation having the highest degree of matching with the first classification item determined based on the information related to the first classification axis in order,
the at least one processor executes the instructions to interrupt acceptance of input of the evaluation information when the evaluation score is lower than a predetermined threshold or when the evaluation score is lower than an evaluation score of the fragrance for evaluation that has been input just before this evaluation score is input by the predetermined threshold or more, and
the at least one processor is configured to control and cause a supply device to supply or discharge the plurality of fragrances in accordance with a control signal that is transmitted to the supply device.

2. The information processing system according to claim 1, wherein the first classification items are items related to the purpose of using the fragrance.

3. The information processing system according to claim 1, wherein the second classification items are items related to a smell quality of the fragrance.

4. The information processing system according to claim 1, wherein the at least one processor executes the instructions to:
determine, for each of the plurality of fragrances, the first classification item of the fragrance based on degrees of matching of the fragrance with the respective items on the first classification axis,
determine, for each of the segments, the fragrance having the highest degree of matching with the first classification item that corresponds to the segment as an expression scent that represents the segment, among the fragrances classified into the segment, and
select expression scents determined for the respective segments that correspond to the first classification item determined based on the information related to the first classification axis and whose second classification items differ from each other to be the fragrances for evaluation.

5. The information processing system according to claim 4, wherein the at least one processor executes the instructions to select the expression scent whose degree of matching with the first classification item determined based on the information related to the first classification axis is equal to or higher than the predetermined threshold to be the fragrance for evaluation.

6. The information processing system according to claim 1, wherein
the at least one processor executes the instructions to determine the fragrance for evaluation having the evaluation score equal to or higher than the predetermined threshold to be the fragrance for presentation.

7. The information processing system according to claim 1, wherein
the at least one processor executes the instructions to determine the fragrance in which fragrances for evaluation having evaluation scores equal to or higher than the predetermined threshold are blended with each other in accordance with the evaluation score to be the fragrance for presentation.

8. The information processing system according to claim 1, wherein the at least one processor executes the instructions to estimate evaluation information of a scent from biological information of the target person.

9. The information processing system according to claim 1, wherein the at least one processor executes the instructions to cause a display input device to display results of analyzing preference, physiological, and psychological responses of the target person based on the evaluation scores.

10. The information processing system according to claim 1, wherein the at least one processor executes the instructions to determine an evaluation order of the fragrances for evaluation by the target person based on the degrees of matching with the first classification item determined in the selection processing, and also based on the attribute information of the target person or usage condition information.

11. The information processing system according to claim 10, wherein the at least one processor executes the instructions to change the order of evaluation of the plurality of fragrances for evaluation after a timing for evaluation of a portion of the plurality of fragrances has ended.

12. The information processing system according to claim 1, wherein the at least one processor executes the instructions to control and cause the supply device to supply the fragrance for evaluation by mixing the air with odorless air at a predetermined ratio.

13. An information processing method for presenting a scent to a target person comprising:
classifying a plurality of fragrances into segments defined corresponding to a combination of one of first classification items on a first classification axis with one of second classification items on a second classification axis;
accepting input of information related to the first classification axis from the target person;
determining one of the first classification items based on the information related to the first classification axis and selecting at least one fragrance for evaluation from each of segments that correspond to the first classification item and whose second classification items differ from each other;
acquiring, for each of the fragrances for evaluation that have been selected, evaluation information of a scent from the target person; and
generating information on a fragrance for presentation to be presented to the target person based on the evaluation information, wherein:
the evaluation information includes evaluation scores, and further comprising:

causing the target person to input evaluation scores of fragrances for evaluation from the fragrance for evaluation having the highest degree of matching with the first classification item determined based on the information related to the first classification axis in order;

interrupting acceptance of input of the evaluation information when the evaluation score is lower than a predetermined threshold or when the evaluation score is lower than an evaluation score of the fragrance for evaluation that has been input just before this evaluation score is input by the predetermined threshold or more; and controlling and causing a supply device to supply or discharge the plurality of fragrances in accordance with a control signal that is transmitted to the supply device.

14. A non-transitory computer readable medium storing a program for presenting a scent to a target person, the program causing a computer to execute:

classification processing for classifying a plurality of fragrances into segments defined corresponding to a combination of one of first classification items on a first classification axis with one of second classification items on a second classification axis;

acquisition processing for accepting input of information related to the first classification axis from the target person;

selection processing for determining one of the first classification items based on the information related to the first classification axis and selecting at least one fragrance for evaluation from each of segments that correspond to the first classification item and whose second classification items differ from each other;

evaluation processing for acquiring, for each of the fragrances for evaluation that have been selected, evaluation information of a scent from the target person; and generation processing for generating information on a fragrance for presentation to be presented to the target person based on the evaluation information, wherein:

the evaluation information includes evaluation scores, and the program causing the computer to further execute:

causing processing for causing the target person to input evaluation scores of fragrances for evaluation from the fragrance for evaluation having the highest degree of matching with the first classification item determined based on the information related to the first classification axis in order;

interrupting processing for interrupting acceptance of input of the evaluation information when the evaluation score is lower than a predetermined threshold or when the evaluation score is lower than an evaluation score of the fragrance for evaluation that has been input just before this evaluation score is input by the predetermined threshold or more; and controlling and causing processing for controlling and causing a supply device to supply or discharge the plurality of fragrances in accordance with a control signal that is transmitted to the supply device.

* * * * *